United States Patent
Shirazi et al.

(10) Patent No.: US 10,584,047 B2
(45) Date of Patent: Mar. 10, 2020

(54) AEROBIC NITRITATION OF AMMONIA AND INTEGRATED ANAMMOX PROCESSES

(71) Applicant: MICROVI BIOTECH INC., Hayward, CA (US)

(72) Inventors: Fatemeh Shirazi, Hayward, CA (US); Ameen Razavi, Fremont, CA (US); Allison Gregg, Dublin, CA (US); Casey McGrath, Oakland, CA (US)

(73) Assignee: MICROVI BIOTECH, INC., Hayward, CA (US)

( * ) Notice: Subject to any disclaimer, the term of this patent is extended or adjusted under 35 U.S.C. 154(b) by 0 days.

(21) Appl. No.: 16/075,051

(22) PCT Filed: Feb. 2, 2017

(86) PCT No.: PCT/US2017/016229
§ 371 (c)(1),
(2) Date: Aug. 2, 2018

(87) PCT Pub. No.: WO2017/136561
PCT Pub. Date: Aug. 10, 2017

(65) Prior Publication Data
US 2019/0039926 A1 Feb. 7, 2019

Related U.S. Application Data

(60) Provisional application No. 62/388,647, filed on Feb. 2, 2016.

(51) Int. Cl.
| | |
|---|---|
| *C02F 3/30* | (2006.01) |
| *C02F 3/00* | (2006.01) |
| *C12N 11/08* | (2006.01) |
| *C12N 11/10* | (2006.01) |
| *C12N 11/14* | (2006.01) |
| C02F 101/16 | (2006.01) |
| C02F 103/34 | (2006.01) |

(52) U.S. Cl.
CPC ............ *C02F 3/307* (2013.01); *C02F 3/006* (2013.01); *C12N 11/08* (2013.01); *C12N 11/10* (2013.01); *C12N 11/14* (2013.01); *C02F 2101/16* (2013.01); *C02F 2103/34* (2013.01); *C02F 2209/001* (2013.01); *C02F 2209/06* (2013.01); *C02F 2209/07* (2013.01); *C02F 2209/22* (2013.01); *C02F 2305/02* (2013.01)

(58) Field of Classification Search
CPC ...... C02F 3/307; C02F 3/006; C02F 2305/02; C02F 2103/34; C02F 2101/16; C02F 2209/22; C02F 2209/07; C02F 2209/06; C02F 2209/001; C12N 11/08; C12N 11/14; C12N 11/10; Y02W 10/15
USPC ............... 210/605, 614, 615, 630, 631, 903; 435/180, 182
See application file for complete search history.

(56) References Cited

U.S. PATENT DOCUMENTS

| | | | |
|---|---|---|---|
| 2012/0085705 A1* | 4/2012 | Theodore | A01G 33/00 210/620 |
| 2014/0367333 A1* | 12/2014 | Razavi-Shirazi | C02F 3/303 210/615 |
| 2017/0332567 A1* | 11/2017 | Gencer | A01K 61/10 |

FOREIGN PATENT DOCUMENTS

| | | | |
|---|---|---|---|
| WO | WO 2011/134011 A1 | * | 11/2011 |
| WO | WO 2015/052279 A1 | * | 4/2015 |

OTHER PUBLICATIONS

Extended Search Report dated Oct. 11, 2019 corresponding to European Patent Application No. 17748162.9, 11 pages.

* cited by examiner

*Primary Examiner* — Fred Prince
(74) *Attorney, Agent, or Firm* — Dentons US LLP

(57) ABSTRACT

Processes are disclosed for the microbial nitritation of ammonia that attenuate the production of at least one of nitrate anion and nitrous oxide. The processes use an ME biocatalyst having a highly porous, hydrophilic polymeric structure with ammonia-oxidizing microorganisms substantially irreversibly retained therein. The processes are particularly useful for integration with anammox processes.

20 Claims, No Drawings

AEROBIC NITRITATION OF AMMONIA AND INTEGRATED ANAMMOX PROCESSES

RELATED APPLICATIONS

Priority is claimed to U.S. Provisional Patent Application 62/388,647, filed Feb. 2, 2016.

FIELD OF THE INVENTION

This invention pertains to aerobic water treatment processes for the nitritation of ammonia using nitrifiers with advantageously low production of at least one of nitrous oxide and nitrate anion, and especially to such processes providing at least about 40 atomic percent of the ammonia nitrogen being bioconverted to nitrite anion.

BACKGROUND

Wastewater streams containing ammonia are provided by a number of sources, including, but not limited to, industrial wastewater streams and municipal wastewater streams. The use of the term ammonia herein is intended to include both ionized ammonia (ammonium cation) and non-ionized ammonia. The equilibrium between ionized and non-ionized ammonia is affected by the composition and pH of the wastewater stream and its environment including, but not limited to, temperature, pressure, and head space gas composition, as is well known in the art.

Due to environmental and public health concerns, removal of ammonia from wastewater streams is desired. One such process for removal of ammonia is by metabolic oxidation using, typically in the presence of *Nitrosomonas* bacteria, to produce nitrate anion which in turn can be removed by microbial denitrification to dinitrogen gas. On a stoichiometric basis, 4½ atoms of oxygen are required for conversion of ammonia to nitrate anion and water. Accordingly, the capital and operating expenses to supply air or other oxygen-containing gas to an ammonia oxidation unit operation can represent a significant expense. Additionally the microbial denitrification process requires the presence of an electron donor, usually organic carbon, for the reduction to dinitrogen gas. Alternatively the ammonia can be oxidized to nitrite anion (nitritation) thus reducing the stoichiometric oxygen requirement. The nitrite anion can then be removed by microbial denitrification to dinitrogen gas.

A further additional proposal is an anoxic metabolic process for ammonium oxidation with nitrite anion as an electron acceptor. This process is sometimes referred to as the anammox process. As can be well appreciated, nearly a quarter of the oxygen required to convert ammonia to nitrate anion can be saved when the ammonia is converted to nitrite anion. This savings in oxygen can sometimes be well over 50 percent when the anammox process is used. The anammox process can be conducted in two separate bioreactors, the first for forming nitrite anion, and the second for the anoxic oxidation of ammonia. Proposals also exist to conduct the anammox process in a single reactor using biofilm or sludge granules containing a region of ammonia oxidizing bacteria and a region of bacteria capable of effecting the anoxic oxidation. This single step anammox process can be challenging in that the ammonia oxidizing bacteria and bacteria capable of effecting the anoxic oxidation of ammonia need to be maintained in balance. Consequently the two step process provides operational advantages.

One challenge that has faced the industry is that the nitritation process, alone or in combination with the anammox process results in the production of nitric oxide and nitrous oxide. These compounds have limited solubility in water and thus are readily exhausted to the atmosphere. The greenhouse effect of nitrous oxide is reported to be about three hundred times that of carbon dioxide. The large volumes of wastewater being processed in a municipal wastewater plant can result in a sizable point source of nitrous oxide emission.

The literature has reported a wide range of productions of nitric oxide and nitrous oxide off gases from wastewater treatment, but there is uniform agreement that the production of nitric oxide is very small in comparison to that of nitrous oxide. Kampschrer, et al., in "Emission of nitrous oxide and nitric oxide from a full-scale single-stage nitritation-anammox reactor", *Water Sci. Technol.*, 60(12), 2009, pages 3211-3217, conclude from their study that the omission of nitrous oxide during normal operation is about 1.23 percent of the nitrogen load to the reactor (1.67 percent of the nitrogen removed). They suggest that implementation of process control parameters may be able to minimize the amount of nitric oxide and nitrous oxide production. The authors indicate that the production of nitrous oxide is increased with increasing nitrite anion concentration. Thus two step nitritation/anoxic oxidation processes would be expected to be more prone to produce nitrous oxide than would single step processes.

Another challenge is minimizing the coproduction of nitrate anion during nitrification, especially using nitrifying microorganisms that are capable of converting nitrite anion to nitrate anion. The coproduction of nitrate anion is particularly problematic for the anammox process in that the nitrate anion is not an effective electron acceptor. If significant co-production of nitrate anion occurs, an additional unit operation may be required to remove nitrate anion before the effluent from the anammox process can be discharged to the environment.

Accordingly processes are sought for the nitritation of ammonia that minimize the emission of nitrous oxide and/or the coproduction of nitrate anion, especially for such processes where the minimization of the emission of nitrous oxide or coproduction of nitrate anion does not require difficult process controls to maintain tight tolerances of, for example, pH and dissolved oxygen. Moreover, processes are sought that enable a high conversion of ammonia to nitrite anion, e.g., at least about 40 atomic percent, and sometimes at least about 70, and preferably at least about 95, atomic percent, of the ammonia nitrogen being converted to nitrite anion, while minimizing nitrous oxide emissions and/or the coproduction of nitrate anion. Such processes would be particularly useful for use with the anammox process.

SUMMARY OF THE INVENTION

In accordance with this invention processes are provided for the nitritation of wastewater containing ammonia while minimizing one or both of nitrous oxide emissions and the coproduction of nitrate anion. The processes are particularly advantageous in that the effluent having a high bioconversion of ammonia to nitrite anion can be achieved while still maintaining extremely low nitrous oxide emissions and low nitrate anion concentrations. Further the processes are not limited to the use of a specific species of ammonia-oxidizing nitrifiers but rather are applicable to the wide variety of microorganisms that are heterotrophic nitrifiers and autotrophic nitrifiers including, but not limited to, bacteria, archaea and fungi.

The processes of this invention use an ME biocatalyst that contains ammonia-oxidizing nitrifier microorganism. ME biocatalysts are disclosed by Shirazi, et al., in United States published patent application 20130337518. The disclosed biocatalysts have:

i. a solid structure of hydrated hydrophilic polymer defining an interior structure having a plurality of interconnected major cavities having a smallest dimension of between about 5 and 100 microns and an HEV of at least about 1000 and ii. a population of microorganisms substantially irreversibly retained in the interior of the solid structure, said population of microorganisms being in a concentration of at least about 60 grams per liter based upon the volume defined by the exterior of the solid structure when fully hydrated, wherein the microorganisms maintain their population substantially stable.

The irreversibly retained microorganisms are believed to undergo phenotypic alterations that enable them, in the biocatalyst of hydrophilic polymer and having interior spacial configurations, to maintain their population substantially stable. Moreover, the biocatalyst has a long lifetime, and competition with undesired microorganism is substantially eliminated making the biocatalyst particularly attractive for treatment of ammonia-containing wastewater that also contains adventitious microorganisms. Additionally, the biocatalysts do not generate appreciable debris from the microorganisms. The ME biocatalysts have been proposed for many processes including, but not limited to, wastewater treatment such as aerobic digestion, anaerobic digestion, phosphorus removal, metal removals, nitrification, and denitrification.

Without wishing to be limited by theory, it is believed that the ME biocatalysts provide microenvironments where any nitrous oxide produced is capable of being further reduced to dinitrogen gas even where the wastewater has a high dissolved oxygen concentration. This, in combination with the high bioactivity provided by the ME biocatalysts, result in very low, if any, emissions of nitrous oxide from the wastewater even when the wastewater may contain adventitious microorganisms that can generate nitrous oxide. The ME biocatalyst are also believed to enhance the tolerance of ammonia oxidizing bacteria to nitrite concentration such that high concentration nitrite-containing effluents can be produced. These high concentration nitrite-containing effluents are advantageous in two step processes for nitritation/anoxic oxidation of ammonia. By using biocatalyst, a substantially stable source of ammonia-oxidizing nitrifier microorganism can be maintained in a basin or bioreactor. For integrated anammox processes (either two step or one step), this stable source of bioactivity facilitates controlling the balance between ammonia and nitrite anion.

In its broad aspects this invention pertains to processes for the nitritation of ammonia in an aqueous medium using ammonia-oxidizing nitrifier microorganisms to bioconvert ammonia comprising:

contacting the aqueous medium under aerobic conditions, preferably at a temperature of from about 0° C. or 3° C. to 50° C., often between about 5° C. and 40° C., with biocatalyst, said biocatalyst comprising:

a. a solid structure of hydrated hydrophilic polymer defining an interior structure having a plurality of interconnected major cavities having a smallest dimension of between 5 and 100 microns and a Hydration Expansion Volume (HEV), which is calculated in volume percent, of 1000 or more, and b. a population of nitrifier microorganisms substantially irreversible retained in the interior structure, said population of microorganisms being in a concentration of about 60 grams or more per liter based upon the volume defined by the exterior of the solid structure when fully hydrated, wherein the microorganisms maintain their population as substantially stable, for a time sufficient to oxidize at least a portion, preferably at least about 40 atomic percent, of the nitrogen in the ammonia to nitrite anion and provide a nitrite-containing effluent and an off-gas, wherein a sufficient amount of biocatalyst is used such that less than about 0.25, preferably less than about 0.1, atomic percent of the converted to ammonia nitrogen is emitted as nitrous oxide into the off-gas.

In preferred aspects of this invention, the oxygen (dissolved oxygen) concentration in the wastewater being contacted with the biocatalyst is between about 1 and 6 or 8 milligrams per liter. In some aspects of this invention, the oxygen concentration in the wastewater is between about 1.5 and 4, say, 2 to 3, milligrams per liter. The ability to effect the ammonia oxidation at low oxygen concentrations reduces the volume of air or other oxygen-containing gas that needs to be supplied to the wastewater. Additionally, these low oxygen concentrations tend to reduce the mole ratio of nitrate anion to nitrite anion in the effluent, and in some instances, this mole ratio is less than about 1:10, preferably less than about 1:20, say, between about 1:200 to 1:50. This low mole ratio of nitrate anion to nitrate anion can be achieved even using nitrifier microorganisms that are capable of oxidizing nitrite anion to nitrate anion.

Another broad aspect of this invention pertains to methods for enhancing the bioactivity of ME biocatalyst containing ammonia oxidizing microorganisms for the nitritation of ammonia-containing aqueous media. In accordance with this broad aspect of the invention, the biocatalyst is contacted with an ammonia-containing aqueous medium under metabolic conditions including the presence of at least about 5, more preferably at least about 6, milligrams of dissolved oxygen per liter of the aqueous medium, for a time sufficient to increase the bioconversion activity of the biocatalyst for nitritation. Typically the duration of the contact with the aqueous medium having the high dissolved oxygen concentration is at least about 30 minutes, and is often in the range of between about 2 hours and 50 hours, say, between about 5 hours and 30 hours. Without wishing to be limited by theory, it is believed the higher oxygen concentrations facilitate the acclimatization of the microorganisms throughout the biocatalyst for nitritation. This higher oxygen treatment can occur when the biocatalyst is first brought in contact with an ammonia-containing aqueous medium or after the biocatalyst has been used for nitritation. Generally, once the biocatalysts have achieved a desired high, bioconversion activity, little, if any, loss of bioconversion activity occurs over the useful life of the biocatalyst, and repeating the higher oxygen treatment provides little, if any, enhancement in a catalyst performance.

Another broad aspect of the invention pertains to the nitritation of ammonia in an aqueous medium using ammonia-oxidizing nitrifier microorganism wherein the mole ratio of nitrate anion to nitrite anion in the effluent is less than about 1:8 even though the dissolved oxygen content of the aqueous medium contains at least about 2, and often at least about 3, milligrams per liter. Since the processes of this aspect of the invention can effectively tolerate high dissolved oxygen concentrations without undue production of nitrate anion, the dissolved oxygen need not be subjected to tight control to avoid undue production of nitrate anion. Thus, diurnal and seasonal changes in flows of, ammonia concentrations in, the influent can readily be accommodated.

In this broad aspect of the invention the duration of contact of the aqueous medium is sufficiently brief that the effluent contains greater than about 1 milligram of ammonium cation per liter. The stable source of bioactivity provided by biocatalyst facilitates controlling the duration of contact within the bioreactor to provide a sought concentration of ammonium cation to be maintained in the effluent. The ability to achieve these desired low ratios of nitrate anion to nitrite anion in the effluent with high dissolved oxygen in accordance with this aspect of the invention also depends upon maintaining the aqueous medium at a sufficiently high pH.

This aspect of the invention proudly pertains to continuous processes for the nitritation of ammonia in an aqueous medium using ammonia-oxidizing nitrifier microorganism comprising:

a. continuously feeding said aqueous medium to at least one bioreaction zone containing biocatalyst wherein said aqueous medium is contacted under aerobic conditions, frequently at least about 2, and more often at least about 3, milligrams of dissolved oxygen per liter, at a temperature of from about 0° C. to 50° C. and at a pH greater than 7 with said biocatalyst to provide a treated aqueous medium containing nitrite anion, said biocatalyst comprising:

i. a solid structure of hydrated hydrophilic polymer defining an interior structure having a plurality of interconnected major cavities having a smallest dimension of between 5 and 100 microns and a Hydration Expansion Volume (HEV), which is calculated in volume percent, of 1000 or more, and ii. a population of microorganism substantially irreversible retained in the interior structure, said population of microorganism being in a concentration of about 60 grams or more per liter based upon the volume defined by the exterior of the solid structure when fully hydrated, wherein the microorganisms maintain their population as substantially stable; and b. continuously withdrawing from said at least one bioreaction zone said treated aqueous medium, wherein the combination of pH of said aqueous medium is sufficiently above 7 and duration of contact of said aqueous medium in the at least one bioreaction zone containing biocatalyst is sufficiently brief that that the treated aqueous medium contains greater than about 1 milligram of ammonium cation per liter to provide a treated aqueous medium having a molar ratio of nitrate anion to nitrite anion less than about 1:8.

The processes of this aspect of the invention can tolerate the presence of high dissolved oxygen concentrations, e.g., up to 7 or 8 or more, milligrams per liter, yet the molar ratio of nitrate anion to nitrite anion can be less than 1:8. The concentration of dissolved oxygen will, of course, be dependent upon the equipment and the process variables employed by the operator. Usually, the dissolved oxygen concentration is in the range of about 2 to 8, and sometimes between about 2.5 or 3 to 5, milligrams per liter. In many operations, it is desired to maintain a low dissolved oxygen concentration to reduce energy costs in introducing oxygen into the bioreaction zone.

The concentration of ammonium cation in the treated aqueous medium is greater than about 1 milligram per liter. Frequently at least about 40 atomic percent of the nitrogen from ammonia in the aqueous medium fed to the bioreaction zone is bioconverted to nitrite anion. Hence, considerable flexibility is provided by the processes of this invention to either partially or nearly completely bioconvert the ammonium cation while still maintaining desirable ratios of nitrate to nitrite anion in the treated aqueous medium. Often the concentration of ammonia in the treated aqueous medium is between about 1 milligram per liter and about 50 or 55 atomic percent of that atomic concentration based on nitrogen of ammonia in the aqueous medium fed to the bioreaction zone.

The bioconversion process increases the acidity of the aqueous medium. The rate of increase will be affected by the amount of bioconversion occurring and the presence of buffers, alkalinity or other pH modifiers present in the aqueous medium. The pH of the aqueous medium is also affected by the initial pH of the aqueous medium as well as any base intermittently or continuously added to the bioreaction zone. The pH of the aqueous medium in the bioreaction zone is preferably greater than 7.3 and can be as high as 9 or more, but is usually in the range of about 7.5 to 8.5. The pH of the treated aqueous medium is also greater than about 7, say, between about 7.2 and 8.5.

The duration of contact in the bioreaction zone can be adjusted in any suitable manner, including, but not limited to, one or more of changing flow rate to the bioreaction zone with a constant volume of biocatalyst to increase or reduce contact time, changing biocatalyst loading in the bioreaction zone, and using two or more bioreaction zones in parallel or in series that are put on or taken off line in response to changes in the flow rate of the aqueous medium to the bioreaction zone and changes to the ammonia concentration in the aqueous medium. Since the biocatalysts used in accordance with this invention retain bioactivity for substantial periods of time in the absence of fresh feed, sequencing two or more bioreaction zones on and off line is a viable mechanism to maintain the sought ammonia concentration in the treated aqueous medium.

In this aspect of the invention, continuous processes are provided the nitritation of ammonia in an aqueous medium using ammonia-oxidizing nitrifier microorganism wherein at least one of the volumetric flow of the aqueous medium and concentration of ammonium cation in said aqueous medium changes over time, comprising:

a. continuously feeding said aqueous medium to one or more bioreaction zones containing biocatalyst wherein said aqueous medium is contacted under aerobic conditions at a temperature of from about 0° C. to 50° C. with said biocatalyst to provide a treated aqueous medium containing nitrite anion, said biocatalyst comprising:

i. a solid structure of hydrated hydrophilic polymer defining an interior structure having a plurality of interconnected major cavities having a smallest dimension of between 5 and 100 microns and a Hydration Expansion Volume (HEV), which is calculated in volume percent, of 1000 or more, and ii. a population of microorganism substantially irreversible retained in the interior structure, said population of microorganism being in a concentration of about 60 grams or more per liter based upon the volume defined by the exterior of the solid structure when fully hydrated, wherein the microorganisms maintain their population as substantially stable; and b. continuously withdrawing from said one or more bioreaction zones said treated aqueous medium, wherein the combination of pH of said aqueous medium is sufficiently above 7 and duration of contact of said aqueous medium in the at least one bioreaction zone containing biocatalyst is controlled such that that the treated aqueous medium contains greater than about 1 milligram of ammonium cation per liter, to provide a treated aqueous medium having a molar ratio of nitrate anion to nitrite anion less than about 1:8.

In yet a further aspect, this invention pertains to integrated nitritation and anammox processes in which the nitritation provides a nitrite-containing aqueous medium for effecting the bioconversion of nitrite anion and ammonium cation to dinitrogen gas. The integration includes all, or part of, an ammonia-containing aqueous medium being subjected to nitritation and then contacted with ammonium cation under anammox conditions with anammox bacteria to produce dinitrogen gas. In one embodiment, the nitritation provides an approximate 1:1 mole ratio of nitrite anion and ammonium cation ("main stream"). In another embodiment, a portion of an ammonia-containing aqueous medium is subjected to nitritation and is recombined with the remaining portion of an ammonia-containing aqueous medium to provide an approximate 1:1 mole ratio of nitrite anion and ammonium cation ("side stream"). In a third embodiment at least a portion, and preferably substantially all, the nitritation occurs in the same reaction zone as the anammox process (one step).

DETAILED DISCUSSION

All patents, published patent applications and articles referenced in this detailed description are hereby incorporated by reference in their entireties.

As used herein, the following terms have the meanings set forth below unless otherwise stated or clear from the context of their use.

The use of the terms "a" and "an" is intended to include one or more of the element described. Lists of exemplary elements are intended to include combinations of one or more of the element described. The term "may" as used herein means that the use of the element is optional and is not intended to provide any implication regarding operability. The use of the term "including" is intended to mean including without limitation.

Adhering to the solid structure of the biocatalyst means that the microorganisms are located in cavities in the interior of the biocatalyst and are substantially irreversibly retained therein although extraordinary conditions and treatments (i.e., not normal bioconversion conditions for bioconversion using the microorganisms) might be able in some instances to cause the microorganism to exit the biocatalyst. Adhering includes surface attachment to the polymer forming the walls of the catalyst as well as where the retained microorganisms are proximate to a polymeric surface, e.g., within about 10 or 20 microns, but not directly contacting the surface. Adhering thus includes physical and electrostatic adherence. In some instances, the polymer used to make the biocatalyst may become embedded in the extracellular polymeric substance around a cell or even in or on the cell wall of the microorganism.

Adventitious microorganisms are microorganisms that may be indigenous to the wastewater or may be introduced into the wastewater from exogenous sources such as microorganisms borne in air or on surfaces with which the wastewater comes in contact or otherwise intentionally or unintentionally introduced.

Alkalinity is the quantitative capacity of an aqueous solution to neutralize an acid and thus measures the sensitivity of the solution to the addition of acid, not the strength of the basicity. Increasing alkalinity can be achieved, for instance, by the addition of carbonate, phosphate, silicate, sulfate, and the like, to an aqueous solution. Alkalinity is quantified herein as the milliequivalents of acid required to neutralize a liter of aqueous medium.

Ammonia-oxidizing nitrifier microorganisms include, but are not limited to ammonia-oxidizing bacteria and ammonia-oxidizing archea.

Biochemical oxygen demand (BOD) is the amount of oxygen required for metabolic conversion of organic carbon in water to carbon dioxide and is an indication of the organic compounds available for food. BOD is reported as milligrams per liter. BOD can be determined by Standard Method 5210B, revision Nov. 16, 1999, as published by the U.S. Environmental Protection Agency.

Bioconversion activity is the rate of consumption of substrate per hour per gram (wet) of microorganism. Where an increase or decrease in bioconversion activity is referenced herein, such increase or decrease is ascertained under similar bioconversion conditions including concentration of substrate and product in the aqueous medium. Bioconversion activity to bioproduct is the rate of production of the bioproduct per hour per gram of microorganism. Bioreactor bioactivity is the rate of consumption of substrate per hour based upon a unit volume of bioreactor and thus may not be the same as bioconversion activity.

Biofilm means an aggregate of microorganisms embedded within an extracellular polymeric substance (EPS) generally composed of polysaccharides, and may contain other components such as one or more of proteins, extracellular DNA and the polymer used to make the biocatalyst. The thickness of a biofilm is determined by the size of the aggregate contained within a continuous EPS structure, but a continuous EPS structure does not include fibrils that may extend between separated biofilms. In some instances, the biofilm extends in a random, three dimensional manner, and the thickness is determined as the maximum, straight line distance between the distal ends. A thin biofilm is a biofilm which does not exceed about 10 microns in any given direction.

Chemical oxygen demand (COD) is the amount of oxygen required to convert organic carbon in water to carbon dioxide and thus is an indication of the organic compound content of the water. COD is reported as milligrams per liter. One procedure for determining COD is Hach Method 8000, February 2009, Ninth Edition.

Dissolved oxygen is oxygen dissolved in the aqueous medium. Determination of dissolved oxygen can be undertaken using calibrated electrochemical instrumental probes as is well known in the art. Where the bioreactor has insufficient mixing to provide a relatively uniform dissolved oxygen concentration in the aqueous medium, e.g., the bioreactor is plug flow, an average of the dissolved oxygen at the point proximate to the input of the oxygen-containing gas and the treated aqueous medium is used as the dissolved oxygen concentration of the bulk aqueous medium in the bioreactor.

A state of essential stasis means that a microorganism population has undergone a substantial cessation of metabolic bioconversion activity but can be revived. The existence of an essential stasis condition can be ascertained by measuring bioconversion activity. The essential stasis condition may be aerobic, anoxic or anaerobic which may or may not be the same as that of normal operating conditions for the microorganism.

An exo-network is a community of spaced-apart microorganisms that can be in the form of individual cells or biofilms that are interconnected by extracellular polymeric substance in the form of strands. The spacing between the microorganisms or biofilms in the exo-network is sufficient to enable the passage of nutrients and substrates there between and is often at least about 0.25, say, at least about 0.5, micron and may be as large as 5 or 10 microns or more.

Exterior skin is an exterior layer of polymer on the biocatalyst that is less open than the major channels in the interior structure of the biocatalyst. A biocatalyst may or may not have a skin. Where a skin is present, it may or may not have surface pores. Where no surface pores are present, fluids diffuse through the skin. Where pores are present, they often have an average diameter of between about 1 and 10 microns.

Fully hydrated means that a biocatalyst is immersed in water at 25° C. until no further expansion of the superficial volume of the biocatalyst is perceived.

The "Hydration Expansion Volume" (HEV) for a biocatalyst is determined by hydrating the biocatalyst in water at 25° C. until the volume of the biocatalyst has stabilized and measuring the superficial volume of the biocatalyst ($V_w$), removing the biocatalyst from water and removing excess water from the exterior, but without drying, and immersing the biocatalyst in ethanol at 25° C. for a time sufficient that the volume of the biocatalyst has stabilized and then measuring the superficial volume of the biocatalyst ($V_s$).

The HEV (which is in volume percent) is calculated as the amount of $[V_w/V_s] \times 100\%$.

To assure dehydration with the ethanol, either a large volume ratio of ethanol to biocatalyst is used or successive immersions of the biocatalyst in fresh ethanol are used. The ethanol is initially dehydrated ethanol.

Highly hydrophilic polymers are polymers to which water is attracted, i.e., are hydroscopic. Often the polymers exhibit, when cast as a film, a water contact angle of less than about 60°, and sometimes less than about 45°, and in some instances less than about 10°, as measured by the sessile drop method using a 5 microliter drop of pure distilled water.

Highly hydrated means that the volume of the biocatalyst (excluding the volume of the microorganisms) is at least about 90 percent water.

Industrial wastewater means water that carries waste from industrial or commercial processes, as distinct from domestic wastewater. These wastes may result from any process or activity of industry, manufacture, trade or business, from the development of any natural resource, or from animal operations such as feedlots, poultry houses, or dairies. The term includes contaminated storm water and also leachate from solid waste facilities.

Intermittent means periodically or at non-periodic intervals.

Irreversibly retained and substantially irreversibly retained mean that the microorganisms are adhering to polymeric structures defining open, porous cavities. Irreversibly retained microorganisms do not include microorganisms located on the exterior surface of a biocatalyst. A microorganism is irreversibly retained even if the biocatalyst has exterior pores of sufficient size to permit egress of the microorganisms.

A matrix is an open, porous, polymeric structure and is an article of manufacture having an interconnected plurality of channels or cavities (herein "major cavities") defined by polymeric structures, said cavities being between about 5 and 100 microns in the smallest dimension (excluding any microorganisms contained therein), wherein fluid can enter and exit the major cavities from and to the exterior of the matrix. The porous matrix may contain larger and smaller channels or cavities than the major cavities, and may contain channels and cavities not open to the exterior of the matrix. The major cavities, that is, open, interconnected regions of between about 5 or 10 to 70 or 100 microns in the smallest dimension (excluding any microorganism contained therein) have nominal major dimensions of less than about 300, preferably less than about 200, microns, and sometimes a smallest dimension of at least about 10 microns. The term open, porous thus refers to the existence of channels or cavities that are interconnected by openings there between.

Municipal wastewater is collected wastewater from two or more sources wherein wastewater is generated by human activity including, but not limited to, human and animal excrement; domestic, commercial, agricultural, mining and industrial wastes and drainage; storm runoff; foodstuffs; and product, intermediate and raw materials disposal. Municipal wastewater typically contains dissolved organics (BOD and COD), solids (Total Suspended Solids, TSS), and various ions including ammonium cation and phosphorus-containing anions.

Permeable means that a component can enter or exit the major cavities from or to the exterior of the biocatalyst.

A phenotypic change or alternation or phenotypic shift is a change in a microorganism's traits or characteristics from environmental factors and is thus different from a change in the genetic make-up of the microorganism.

Population of microorganisms refers to the number of microorganisms in a given volume and include substantially pure cultures and mixed cultures.

Quiescent means that the aqueous medium in a biocatalyst is still; however, flows of nutrients and substrates and bioproducts can occur through the aqueous medium via diffusion and capillary flow.

Retained solids means that solids are retained in the interior of the biocatalyst. The solids may be retained by any suitable mechanism including, but not limited to, restrained by not being able to pass through pores in the skin of a biocatalyst, by being captured in a biofilm or a polysaccharide structure formed by microorganisms, by being retained in the polymeric structure of the biocatalyst, or by being sterically entangled within the structure of the biocatalyst or the microorganisms.

Smallest dimension means the maximum dimension of the shortest of the maximum dimensions defining the length, width and height of a major cavity. Usually a preponderance of the major cavities in a matrix are substantially width and height symmetrical. Hence the smallest dimension can be approximated by the maximum width of a cavity observed in a two dimensional cross section, e.g., by optical or electronic microscopy.

A solubilized precursor for the polymer is a monomer or prepolymer or the polymer itself that is dissolved or dispersed such that solids cannot be seen by the naked eye and is stable. For instance, a solid can be highly hydrated and be suspended in an aqueous medium even though the solid is not dissolved.

A stable population of microorganisms means that the population of microorganisms does not decrease by more than 50 percent nor increase by more than 400 percent.

The wet weight or wet mass of cells is the mass of cells from which free water has been removed, i.e., are at the point of incipient wetness. All references to mass of cells is calculated on the basis of the wet mass of the cells.

References to organic acids herein shall be deemed to include corresponding salts and esters.

References to matrix dimensions and volumes herein are of fully hydrated matrices unless otherwise stated or clear from the context.

For the purposes of the following discussion, the ammonia oxidizing microorganisms will from time to time be referred to as microorganisms.

Process

The ammonia-containing aqueous medium to be treated (sometimes herein referred to as "raw water stream") may be derived from any suitable source including, but not limited to, municipal wastewater and industrial wastewater. The wastewater may be directly used as the ammonia-containing aqueous medium, or may be subjected to one or more unit operations such as, but not in limitation, solids separation and aerobic oxidation of organic compounds if present in the wastewater stream. Thus, the wastewater can be primary or secondary effluent in a municipal wastewater plant. Often, the ammonia-containing aqueous medium contains at least about 10 milligrams of ammonia (ammonium cation and non-ionized ammonia) per liter calculated as nitrogen (sometimes herein referred to as "ammonia loading concentration"). The ammonia loading concentration will vary depending upon the source of the raw water stream, and for a given raw water stream, the ammonia loading concentration can vary over time, e.g., due to changes in industrial operation or due to the diurnal and seasonal fluctuations associated with, e.g., raw water passing to municipal wastewater plants. For industrial raw water streams, the ammonia loading concentration can range up to about 10,000 or more milligrams (calculated as N) per liter, say, between about 10 to 5000 milligrams (calculated as N) per liter. Typical municipal wastewater has an ammonia loading concentration of between about 15 or 20 to 100 or more milligrams (calculated as N) per liter. Anaerobic digesters often provide effluents containing between about 500 to 5000 milligrams of ammonia (calculated as N) per liter.

Advantages of the processes of this invention include, but are not limited to, the ability to effect nitritation of high-strength ammonia-containing aqueous media and to rapidly respond to wide fluctuations in ammonia loading concentration and wastewater flow rates while still achieving sought nitritation and avoiding the production of undue amounts of nitrate anion and minimizing nitrous oxide emissions. Particularly when the treated water is to be used for anaerobic ammonia oxidation to produce dinitrogen gas, the ability to maintain a low nitrate anion concentration is beneficial as nitrate anion is not consumed during an anaerobic oxidation. If the nitrate anion concentration can be maintained sufficiently low, a subsequent treatment to remove nitrate anion can be avoided. Also, the consumption of ammonia and other energy or nutrient sources by the ME biocatalyst typically retards the rate of growth of the population of adventitious microorganisms in the aqueous medium.

In some instances the raw water stream contains adventitious microorganisms. Typically, the presence of these adventitious microorganisms is not unduly deleterious to the processes this invention. The ME biocatalyst can be used in an amount such that, due to its substantial bioconversion activity, the preponderance of the ammonia oxidation is effected by the ME biocatalyst. The adventitious microorganisms would oxidize a minor portion of the ammonia, and hence, their contribution to nitrate anion or nitrous oxide production is attenuated. It is thus possible to provide an effluent having relatively high nitrite anion concentration and very little nitrate anion concentration. As discussed later, these other microorganisms might be purposefully provided or allowed to exist if they are to be used for further conversions of the ammonia and nitrate anion to dinitrogen gas. Preferably nitrate anion is produced in an amount less than about 10 atomic percent of the ammonia nitrogen converted during nitritation. In some instances less than about 5, and preferably less than about 1, atomic percent of the ammonia nitrogen is converted to nitrate anion. In some aspects of this invention, the mole ratio of nitrite to nitrate anion is less than about 1:8, and more preferably less than about 1:10, and sometimes less than about 1:20.

The ammonia-containing aqueous medium being treated contains oxygen for the oxidation of ammonia to nitrite anion. Where the ammonia-containing aqueous medium contains organic carbon, the oxygen supply should be sufficient to enable bioconversion of organic carbon to carbon dioxide. Usually, substantial consumption of the organic carbon occurs prior to the nitritation. Many of the ME biocatalysts used in the processes of this invention have the capability of metabolically oxidizing the organic carbon as well as effecting the ammonia oxidation to nitrite anion. Any suitable source of oxygen can be used such as air, oxygen-enriched air and substantially pure oxygen. Typically the oxygen concentration (dissolved oxygen) in the ammonia-containing aqueous medium is between about 1 and 6 or 8 milligrams per liter. In some instances, the oxygen concentration in the wastewater is between about 1.5 and 4, say, 2 to 3, milligrams per liter. The oxygen may be introduced into the ammonia-containing aqueous medium prior to the contact with the biocatalyst and/or intermittently or continuously during contact with the biocatalyst. Any suitable unit operation for introducing oxygen into the ammonia-containing aqueous medium can be used.

Depending upon the type of bioreactor, the dissolved oxygen concentration can be relatively uniform in the aqueous medium or can vary, such as with bioreactors having more plug flow properties, as the oxygen is consumed in the bioconversions. The nitritation effluent, if desired, can have a relatively low oxygen content which facilitates its use in anoxic unit operations such as anaerobic oxidation of ammonia (anammox). The low oxygen concentration can also enable anaerobic ammonia oxidation in the same bioreactor using an anammox biocatalyst. However, an advantage is that low nitrate anion production can be achieved even in the presence of higher dissolved oxygen concentrations.

The temperature for the nitritation depends upon the type of microorganism employed. Mesophilic microorganisms require lower temperatures then do thermophilic microorganisms. Most nitrifiers are mesophilic and thus operable under ambient temperatures in many wastewater treating facilities. Since the ME biocatalysts maintain a steady population of microorganisms, temperatures required for population growth of microorganisms are not required. Accordingly, for mesophilic nitrifier microorganisms lower temperatures, say, from about 0° C. or 3° C. to 15° C. can be employed while still achieving desirable bioconversion activity.

The ammonia-containing aqueous medium can be of any suitable pH during the contacting with the ME biocatalyst. It should be understood that the pH of the aqueous medium will affect the ratio between ammonium cation and non-ionized ammonia in the aqueous medium. Often the pH of the aqueous medium is between about 4 and 8 or 9 or more. In certain aspects of the invention, the pH of the aqueous medium is greater than about 7 to facilitate maintaining a low mole ratio of nitrate to nitrite anion ratio. The ammonia-containing aqueous medium may inherently provide the sought pH, if not, the pH may be maintained by the intermittent or continuous addition of base. Any suitable base can be used, including, but not limited to, one or more of sodium hydroxide, calcium hydroxide and calcium oxide. In some instances the ammonia-containing aqueous medium has an alkalinity greater than about 20, say, greater than about 50, e.g., between about 75 and 1000 or more, milliequivalents per liter.

The duration of the contact between the ammonia-containing aqueous medium and the ME biocatalyst will depend upon the concentration of ammonia in the aqueous medium to be treated; the presence, if any, of organic carbon that must be metabolized; the sought conversion of ammonia to nitrite anion; the bioconversion activity of the ME biocatalyst under the metabolic conditions used for the ammonia oxidation; the density of the ME biocatalyst in the bioreactor; the presence and population of adventitious microorganisms in the bioreactor, and the like. While durations of contact may be as long as 20 or 30 hours or more, frequently the use of the ME biocatalyst enables hydraulic residence times of less than about 5 or 6 hours to be used, and most often between about 0.01 and 4 hours. Where lower nitrous oxide is sought, shorter hydraulic residence times are desired.

The duration of the contact will affect the concentration of ammonium cation in the treated aqueous medium. In some instances the flow of wastewater to the bioreactor is variable. For instance, municipal wastewater facilities experience a diurnal flow range of up to four fold. Moreover, rain, snow melt, and the like can further increase the flow to a municipal wastewater facility. The ME biocatalyst enhances the robustness of the microorganisms irreversibly retained therein such that bioactivity can be quickly reestablished when needed. It should be noted that the net production of sludge, e.g., from indigenous or adventitious microorganisms, is not materially affected by variations in flow of wastewater to the bioreactor as the high bioactivity provided by the ME biocatalysts provides for very low hydraulic retention times. The duration of contact can be adjusted in any suitable manner, including, but not limited to, one or more of changing flow rate to increase or reduce contact time, changing biocatalyst loading, and using two or more reaction zones in parallel or in series that are put on or taken off line. Usually in the nitritation processes of this invention, of the ammonia oxidized, at least about 90 percent, and preferably at least about 95 percent to essentially all, is nitrite anion (calculated on an atomic N basis). The nitrous oxide emissions are preferably less than about 0.25, preferably less than about 0.1, and in some instances less than about 0.05, percent of the oxidized ammonia nitrogen (calculated on an atomic N basis). The emissions of nitric oxide are generally extremely low, often below about 0.01 percent of the oxidized ammonia nitrogen (calculated on an atomic N basis).

The nitritation in accordance can be a batch, semi-batch or, preferably, continuous operation.

The nitritation of the ammonia-containing aqueous medium is conducted in a bioreactor. The bioreactor may be of any suitable type. Bioreactors include up-flow and down-flow packed bioreactors, trickle bed bioreactors, ponds, bubble column bioreactors, stirred bioreactors, fluidized bed bioreactors, plug flow (tubular) bioreactors, rotating disc bioreactors and membrane bioreactors. The biocatalyst can be freely mobile in the wastewater being treated or fixed, e.g., to a structure in the reactor vessel, or can itself provide a fixed structure. Often the biocatalyst comprises less than about 50, and sometimes between about 5 and 40, volume percent of the bioreactor volume.

More than one reactor vessel or stage can be used in a bioreactor. For instance, reactor vessels may be in parallel or in sequential flow series. In some instances, a bioreactor containing a plurality of vessels or stages with fluid intermixing there between are desired. In such instances, at least 2, and sometimes between about 3 and 20, stages are used. Where the bioreactor comprises a fluidized bed bioreactor, the density of the ME biocatalyst in each stage may be selected to efficiently circulate therein.

Where more than one stage is used in a bioreactor, the metabolic conditions in each stage may be the same or different. Where the ME biocatalyst is mobile, screens or other separation units such as gravity separators, can be used to prevent flow of ME biocatalyst from one stage to another. In some instances, ME biocatalyst may be permitted to pass from one stage to a subsequent stage, then separated from the treated wastewater and recycled to the prior stage, e.g., using separation unit operations as described above.

In preferred embodiments using tank-type bioreactors, the bioreactor is adapted to provide agitation by one or more of mechanical means or flow of the wastewater or by the passage of air or other oxygen-containing gas through the wastewater in the bioreactor. The agitation enhances mixing of the wastewater and, in the event that the ME biocatalyst is particulate, mitigates against compaction of the particles. The processes of this invention are useful in deeper bioreactors. The deeper the bioreactor, the more mass that is required to be suspended. In typical free cell systems, agglomerations of solids are generated which must be suspended. This results in a balance between the depth of the bioreactor and the cost of air supply, and hence, typical free cell suspension aerobic bioreactors do not have depths greater than about 10 meters. Increased depth is advantageous both in terms of capital costs and footprint and in terms of additional contact time with air for mass transfer of oxygen.

It is to be understood that the nitrite anion produced can be further treated, e.g., by microbial denitrification, to reduce nitrite anion to dinitrogen, and the reduction equivalents can be provided by organic electron donors such as organic waste, carbohydrates, carboxylates, and alcohol, or by ammonia, which is oxidized, to produce dinitrogen. The denitrification can be performed in an anoxic reactor containing denitrifying bacteria or can be performed by interrupting the oxygen supply to alternate between toxic and anoxic conditions. Oxygen-limiting conditions can be used where the oxygen consumption by microorganisms for nitrification generate anoxic conditions for the reduction of nitrate anion. Where oxygen-limiting conditions are used, it is believed that regions of lower oxygen concentration exist within the bioreactor.

Typically, denitrification is conducted at a temperature between about 5° C. and 40° C. and a pH between about 4 and 9. Generally the oxygen concentration for anoxic conditions is less than about 1, preferably less than about 0.5, milligrams per liter. Where oxygen-limiting conditions are used, the oxygen concentration is often less than about 2, preferably less than about 1.5, milligrams per liter. Typical denitrifying microorganisms include species of *Pseudomonas, Achromobacter, Bacillus* and *Micrococcus* such as *Paracoccus denitrificans, Thiobacillus denitrificans*, and *Micrococcus denitrificans*. Microorganisms that can anaerobically oxidize ammonia using nitrite anion include, but are not limited to, planctomycete bacteria such as genera *Brocadia, Kuenenia, Anammoxoglobus, Jettenia*, and *Scalindua*.

The processes of this invention are preferably associated with anaerobic ammonia oxidation unit operations to convert ammonia and nitrite anion to dinitrogen gas (anammox process). With low production of nitrate anion during nitritation, the effluent from the anaerobic ammonia oxidation unit operation (anammox process) is sometimes below about 10, preferably less than about 5, milligrams of total nitrogen per liter.

Where the processes this invention are associated with anaerobic ammonia oxidation unit operations, several process schemes or options exist. In a first option, the entire ammonia-containing aqueous medium is sequentially passed to a nitritation unit operation in accordance with processes of this invention and then to an anaerobic ammonia oxidation unit operation. In this option the hydraulic retention time in the nitritation unit operation is varied to provide a mole ratio of nitrite to ammonia of about 1:1, say, about 0.9:1 to 1:1.1, in the nitritation unit operation. In a second option, the ammonia-containing aqueous medium is split into two streams, one of which is passed to a nitritation unit operation, and the other of which is combined with the effluent from the nitritation unit operation, and the combined stream is passed to an anaerobic ammonia oxidation unit operation. The split of the two streams is such that the combined stream passing to the anaerobic ammonia oxidation unit operation has a mole ratio of nitrite to ammonia of about 1:1, say, about 0.9:1 to 1:1.1. In a third option, an effluent from a nitritation unit operation, which effluent contains ammonia, is passed to a single stage anammox unit operation in which nitrite anion is produced from at least the ammonia in the effluent from the nitritation unit operation and anaerobic ammonia oxidation occurs. In this option, the ammonia-containing aqueous medium is split such that a sufficient portion is directed to the nitritation unit operation to meet any shortfall and nitrite anion production in the anammox unit operation. With respect to the second and third options the processes of this invention can be used to provide an effluent from the nitritation unit operation in which the nitrite anion comprises at least about 75 or 80 percent, and in some instances between 90 percent and essentially all, of the total nitrogen (calculated on an atomic N basis). It is to be understood that each unit operation may comprise one or more bioreactors and recycling streams between bioreactors can occur.

ME Biocatalyst

A. ME Biocatalyst Overview

The ME biocatalysts have a polymeric structure (matrix) defining interconnected major cavities, i.e., are open, porous matrices, in which the microorganisms are metabolically retained in the interior of the matrices, that is, the microorganisms promote the adherence rather than being physically restrained by an external structure. In the biocatalysts of this invention, the microorganisms and their communities, inter alia, regulate their population. Also, in conjunction with the sensed nature of the microenvironment in the matrices, it is believed that the microorganisms establish a spatial relationship among the members of the community.

The microorganisms that are retained in the matrices have the ability to form an exo-network. The quiescent nature of the cavities facilitate forming and then maintaining any formed exo-network. A discernable exo-network is not believed essential to achieving phenotypic alterations in the microorganism population such as population modulation and metabolic shift. Where an exo-network develops, often strands of EPS interconnect proximate microorganisms and connect microorganisms to the surface and form the exo-network. In some instances, the microorganisms form thin biofilms and these thin biofilms are encompassed in the exo-network. The biocatalysts have a substantial absence of biofilms in their interiors that are larger than thin biofilms. Hence, any biofilms that may ultimately form in the biocatalysts are relatively thin, e.g., up to about 10, and preferably up to about 2 or 5, microns in thickness, and stable in size. Thus, each thin biofilm is often only a few cells and is connected in an exo-network.

Communication among the microorganisms is believed to occur through emitting chemical agents, including, but not limited to, autoinducers, and communication includes communications for community behavior and for signaling. Often, the preparation of the biocatalysts used in the processes of this invention can result in a population of microorganisms being initially located in the interior of the biocatalyst that is substantially that which would exist at the steady-state level. At these densities of microorganisms in the biocatalysts, community communications are facilitated which are believed to commence during the formation of the biocatalysts, and phenotypic shifts occur to enable the metabolic retention and modulate the population of microorganisms.

Another phenotypic alteration occurring in the biocatalysts, which is believed to be a result of this communication, is a metabolic shift, i.e., the metabolic functions of the community towards reproduction are diminished and the sought bioconversion continues. The population of microorganisms in the biocatalyst may tend to have an old average age due to this shift in the metabolic activity. Older microorganisms also tend to provide a more robust and sustainable performance as compared to younger cells as the older cells have adapted to the operating conditions.

Additional benefits of this communication can be an increase in community-level strength or fitness exhibited by the community in warding off adventitious microorganisms and maintaining strain-type uniformity. In some instances, the microorganisms during use of the biocatalyst may undergo natural selection to cause the strain-type in the community to become heartier or provide another benefit for the survival of the community of microorganisms. In some instances, the communication among the microorganisms may permit the population of microorganisms to exhibit multicellularity or multicellular-like behaviors. Thus the population of microorganisms in a biocatalyst of this invention may have microorganisms adapting to different circumstances but yet working in unison for the benefit of the community.

In some instances the porous matrix may provide modulation of the substrate and nutrients to the microorganisms to effect to optimize metabolic pathways involving substrates that are available, and these pathways may or may not be the primarily used pathways where ample substrate and other nutrients are available. Accordingly, microorganisms in the biocatalysts may exhibit enhanced bioconversion activity for a primarily used pathway or metabolic activity that is normally repressed.

It is also believed that the microenvironments may promote genetic exchange or horizontal gene transfer. Conjugation or bacterial mating may also be facilitated, including the transfer of plasmids and chromosomal elements. Moreover, where microorganisms lyse, strands of DNA and RNA in the microenvironments are more readily accessible to be taken up by microorganisms in these microenvironments. These phenomena can enhance the functional abilities of the microorganisms.

The ME biocatalysts exhibit an increased tolerance to toxins. In some instances, communications among microorganisms and the exo-network may facilitate the population establishing defenses against toxins. The community response to the presence of toxins has been observed in the biocatalysts of this invention. For instance, the biocatalysts survive the addition of toxins such as ethanol and sodium hypochlorite and the original bioconversion activity is quickly recovered thus indicating the survival of essentially the entire community.

In summary, due to the microenvironments in the ME biocatalyst, communication among the microorganisms and the phenotypic alterations undergone by the microorganisms, the biocatalysts provide a number of process-related advantages including, but not limited to,

- no solid debris being generated,
- the potential for high densities of bioactive material in a bioreactor,
- stable population of microorganisms and bioactivity over extended periods of time,
- metabolic shift of microorganisms towards the bioconversion rather than growth and carbon flow shift,
- ability of microorganisms to undergo essential stasis for extended durations,
- ability to quickly respond to changes in substrate rate of supply and concentration,
- attenuation of diauxic growth,
- enhanced control and modulation of pH and redox balances in the microenvironment of the biocatalyst,
- greater tolerance to substrate, bioproduct and contaminants,
- ability to bioconvert substrate at ultralow concentrations,
- ability to use slower growing and less robust microorganisms and increased resistance to competitiveness,
- enhanced microorganism strain purity capabilities,
- ability to be subjected to in situ antimicrobial treatment,
- ability to quickly start a bioreactor since the density of bioactive material required at full operation is contained in the biocatalyst, and
- ease of separation of bioproduct from biocatalyst thereby facilitating continuous operations.

If desired, the biocatalysts may be treated to enhance the formation of the exo-network, and if desired, thin biofilms, prior to use in the metabolic process. However, performance of the porous matrices is not generally dependent upon the extent of exo-network formation, and often bioconversion activities remain relatively unchanged between the time before the microorganisms have attached to the polymeric structure and the time when extensive exo-network structures have been generated.

B. Physical Description of the ME Biocatalysts

The ME biocatalysts comprise a matrix having open, porous interior structure with bioactive material irreversibly retained in at least the major cavities of the matrix.

The matrices may be a self-supporting structure or may be placed on or in a preformed structure such as a film, fiber or hollow fiber, or shaped article. The preformed structure may be constructed of any suitable material including, but not limited to, metal, ceramic, polymer, glass, wood, composite material, natural fiber, stone, and carbon. Where self-supporting, the matrices are often in the form of sheets, cylinders, plural lobal structures such as trilobal extrudates, hollow fibers, or beads which may be spherical, oblong, or free-form. The matrices, whether self-supporting or placed on or in a preformed structure, preferably have a thickness or axial dimension of less than about 5, preferably less than about 2, say, between about 0.01 to 1, centimeters.

The porous matrices may have an isotropic or, preferably, an anisotropic structure with the exterior portion of the cross section having the densest structure. The major cavities, even if an anisotropic structure exists, may be relatively uniform in size throughout the interior of the matrix or the size of the major cavities, and their frequency, may vary over the cross-section of the biocatalyst.

The biocatalyst has major cavities, that is, open, interconnected regions of between about 5 or 10 to 70 or 100 microns in the smallest dimension (excluding any microorganisms contained therein). For the purposes of ascertaining dimensions, the volume of the microorganisms includes any mass in the exo-network. In many instances, the major cavities have nominal major dimensions of less than about 300, preferably less than about 200, microns, and sometimes a smallest dimension of at least about 10 microns. Often the biocatalyst contains smaller channels and cavities which are in open communication with the major cavities. Frequently the smaller channels have a maximum cross-sectional diameter of between about 0.5 to 20, e.g., 1 to 5 or 10, microns. The cumulative volume of major cavities, excluding the volume occupied by microorganisms and mass associated with the microorganisms, to the volume of the biocatalyst is generally in the range of about 40 or 50 to 70 or 99, volume percent. In many instances, the major cavities constitute less than about 70 percent of the volume of the fully hydrated catalyst with the remainder constituting the smaller channels and pores. The volume fraction of the biocatalyst that constitute the major cavities can be estimated from its cross-section. The cross section may be observed via any suitable microscopic technique, e.g., scanning electron microscopy and high powered optical microscopy. The total pore volume for the matrices can be estimated from the volumetric measurement of the matrices and the amount and density of polymer, and any other solids used to make the matrices.

The ME biocatalyst is characterized by having high internal surface areas, often in excess of at least about 1 and sometimes at least about 10, square meter per gram. In some instances, the volume of water that can be held by a fully hydrated biocatalyst (excluding the volume of the microorganisms) is in the range of 90 to 99 or more, percent. Preferably the biocatalyst exhibits a Hydration Expansion Volume (HEV) of at least about 1000, frequently at least about 5000, preferably at least about 20,000, and sometimes between 50,000 and 200,000, percent.

Usually the type of polymer selected and the void volume percent of the matrices are such that the matrices have adequate strength to enable handling, storage and use in a bioconversion process.

The porous matrices may or may not have an exterior skin. Preferably the matrices have an exterior skin to assist in modulating the influx and efflux of components to and from the interior channels of the porous matrix. Also, since the skin is highly hydrophilic, and additional benefit is obtained as contaminating or adventitious microorganisms have difficulties in establishing a strong biofilm on the exterior of the biocatalyst. These contaminating microorganisms are often subject to removal under even low physical forces such as by the flow of fluid around the biocatalysts. Thus, the fouling of the biocatalyst can be substantially eliminated or mitigated by washing or by fluid flows during use.

Where present, the skin typically has pores of an average diameter of between about 1 and 10, preferably 2 to 7, microns in average diameter. The pores may comprise about 1 to 30, say, 2 to 20, percent of the external surface area. The external skin, in addition to providing a barrier to entry of adventitious microorganisms into the interior of the biocatalyst, is preferably relatively smooth to reduce the adhesion of microorganisms to the external side of the skin through physical forces such as fluid flow and contact with other solid surfaces. Often, the skin is substantially devoid of anomalies, other than pores, greater than about 2 or 3 microns. Where a skin is present, its thickness is usually less than about 50, say, between about 1 and 25, microns. It should be understood that the thickness of the skin can be difficult to discern where the porous matrix has an anisotropic structure with the densest structure being at the exterior of the matrix.

A high density of microorganisms can exist at steady-state operation within the ME biocatalysts. The combination of the flow channels and the high permeability of the polymeric structure defining the channels enable viable microorganism population throughout the matrix, albeit with a plurality of unique microenvironments and nano-environments. In some instances, when the bioactive material comprises microorganisms, the cell density based upon the volume of the matrices is at least about 100 grams per liter, preferably at least about 150 or 200, and often between about 250 and 750, grams per liter.

Solid-Containing ME Biocatalysts

The ME biocatalysts may contain one or more particulate solids which can be used to provide a sought density of the ME biocatalyst. The solid, if desired, may be a solid sorbent. The solid may be the hydrophilic polymer forming the structure or may be a particulate, i.e., a distinct solid structure regardless of shape, contained in the solid structure. Where the solid serves as a sorbent, it may be any suitable solid sorbent for the substrate or nutrients or other chemical influencing the sought metabolic activity such as, but not limited to, co-metabolites, inducers, and promoters or for components that may be adverse to the microorganisms such as, and not in limitation, toxins, phages, bioproducts and by-products. The solid sorbent is typically an adsorbent where the sorption occurs on the surface of the sorbent.

The particulate solids can be used to adjust the density of the ME biocatalyst in the form of discrete particles to facilitate the separation of the biocatalysts from the treated wastewater. Where the ME biocatalysts are sought to be in a bed expanded or fluidized, the density of the ME biocatalysts is typically designed to be in the range of between about 1.05 to 1.2, say, 1.1 to 1.15, grams per cubic centimeter.

The particulate solids are preferably nano materials having a major dimension less than about 5 microns, preferably, between about 5 nanometers to 3 microns. Where the solid is composed of polymer, the solid structure may be essentially entirely composed of the polymer or may be a block copolymer or polymeric mixture constituting between about 5 and 90 mass percent of the solid structure (excluding water). Where the solid is a separate particulate in the biocatalyst, the biocatalyst may comprise between about 5 to 90 mass percent of the mass of the biocatalyst (excluding water and microorganisms but including both the hydrophilic polymer and the particulates). More than one solid may be used in a biocatalyst. Preferably the solid is relatively uniformly dispersed throughout the interior of the biocatalyst although the solid may have a varying distribution within the biocatalyst. Where the distribution varies, the regions with the higher concentration of solid often are found toward the surface of the biocatalyst.

Examples of solids include, without limitation, polymeric materials, especially with polar moieties, carbon (including but not limited to activated carbon), silica (including but not limited to fumed silica), silicates, clays, molecular sieves, and the like. The molecular sieves include, but are not limited to zeolites and synthetic crystalline structures containing oxides and phosphates of one or more of silicon, aluminum, titanium, copper, cobalt, vanadium, titanium, chromium, iron, nickel, and the like. The sorptive properties may comprise one or more of physical or chemical or quasi-chemical sorption on the surface of the solid sorbent. Thus, surface area and structure may influence the sorptive properties of some solid sorbents. Frequently the solid sorbents are porous and thus provide high surface area and physical sorptive capabilities. Often the pores in the solid sorbents are in the range of about 0.3 to 2 nanometers in effective diameter.

The solids may be incorporated into the polymeric structure in any convenient manner, preferably during the preparation of the ME biocatalyst.

Enzyme-Containing ME Biocatalysts

In another aspect, the ME biocatalysts can contain, in addition to the microorganisms, one or more extracellular enzymes in the interior of the biocatalyst to cause a catalytic change to a component which may be substrate or other nutrients, or a bioproduct or by-product or co-product of the microorganisms, or may be a toxin, phage or the like. Typically extracellular enzymes bond or adhere to solid surfaces, such as the hydrophilic polymer, solid additives, cell walls and extracellular polymeric substance. Hence, the enzymes can be substantially irreversibly retained in the interior of the biocatalyst. Due to the structure of the biocatalysts of this invention, the microorganisms and the enzymes can be in close proximity and thus effective, cooperative bioconversions can be obtained. The association of the enzymes with the interior surfaces of the biocatalyst typically increases the resistance of the enzyme or enzymes to denaturation due to changes in temperature, pH, or other factors related to thermal or operational stability of the enzymes. Also, by being retained in the biocatalyst, the use of the enzyme in a bioreactor is facilitated and undesirable post-reactions can be mitigated.

The enzymes may be bound to the precursor for the hydrophilic polymer of the biocatalyst prior to the formation of the biocatalyst or may be introduced during the preparation of the biocatalyst, e.g., by addition to the liquid medium for forming the biocatalyst. There are many methods that would be known to one of skill in the art for providing enzymes or fragments thereof, or nucleic acids, onto a solid support. Some examples of such methods include, e.g., electrostatic droplet generation, electrochemical means, via adsorption, via covalent binding, via cross-linking, via a chemical reaction or process. Various methods are described in Methods in Enzymology, Immobilized Enzymes and Cells, Part C. 1987. Academic Press. Edited by S. P. Colowick and N. O. Kaplan. Volume 136; Immobilization of Enzymes and Cells. 1997. Humana Press. Edited by G. F. Bickerstaff. Series: Methods in Biotechnology, Edited by J. M. Walker; DiCosimo, R., McAuliffe, J., Poulose, A. J. Bohlmann, G. 2012. Industrial use of immobilized enzymes. Chem. Soc. Rev.; and Immobilized Enzymes: Methods and Applications. Wilhelm Tischer and Frank Wedekind, Topics in Current Chemistry, Vol. 200. Page 95-126.

C. Methods for Making ME Biocatalysts

The components, including bioactive materials, used to make the ME biocatalysts and the process conditions used for the preparation of the biocatalysts are not critical to the broad aspects of this invention and may vary widely as is well understood in the art once understanding the principles described above. In any event, the components and process conditions for making the biocatalysts with the irreversibly, metabolically retained microorganisms should not adversely affect the microorganisms.

The ME biocatalysts may be prepared from a liquid medium containing the bioactive material and solubilized precursor for the hydrophilic polymer which may be one or more of a polymerizable or solidifiable component or a solid that is fusible or bondable to form the matrix. Aqueous media are most often used due to the compatibility of most microorganisms and enzymes with water. However, with bioactive materials that tolerate other liquids, such liquids can be used to make all or a portion of the liquid medium. Examples of such other liquids include, but are not limited to liquid hydrocarbons, peroxygenated liquids, liquid carboxy-containing compounds, and the like. Mixed liquid media can also be used to prepare the biocatalyst. The mixed media may comprise miscible or immiscible liquid phases. For instance, the bioactive material may be suspended in a dispersed, aqueous phase and the polymerizable or solidifiable component may be contained in a continuous solvent phase.

The liquid medium used to prepare the ME biocatalyst may contain more than one type of microorganism, especially where the microorganisms do not significantly compete for the same substrate, and may contain one or more isolated enzymes or functional additives such as polysaccharide, solid sorbent and phosphorescent materials, as described above. Preferably, the biocatalysts contain a single type of microorganism. The concentration of the microorganisms in the liquid medium used to make the biocatalysts should at least be about 60 grams per liter. As discussed above, the concentration of microorganisms should preferably approximate the sought density of microorganisms in the biocatalyst. The relative amounts of microorganism and polymeric material in forming the biocatalyst can vary widely. The growth of the population of microorganisms post formation of the biocatalyst is contemplated as well as the potential for damage to some of the population of microorganisms during the biocatalyst-forming process. Nevertheless, higher microorganism concentrations are generally preferred, e.g., at least about 100 or 150 grams per liter, preferably at least about 200, and often between about 250 and 750, grams per liter of the liquid medium used to make the biocatalysts.

Any suitable process may be used to solidify or polymerize the polymeric material or to adhere or fuse particles to form the open, porous polymeric matrix with microorganism irreversibly retained therein. The conditions of suitable processes should not unduly adversely affect the microorganisms. As microorganisms differ in tolerance to temperatures, pressures and the presence of other chemicals, some matrix-forming processes may be more advantageous for one type of microorganism than for another type of microorganism.

Preferably the polymeric matrix is formed from solidification of a high molecular weight material, by polymerization or by cross-linking of prepolymer in manner that a population of microorganisms is provided in the interior of the biocatalyst as it is being formed. Exemplary of processes include solution polymerization, slurry polymerization (characterized by having two or more initial phases), and solidification by cooling or removal of solvent.

The biocatalysts may be formed in situ in the liquid medium by subjecting the medium to solidification conditions (such as cooling or evaporation) or adding a component to cause a polymerization or cross-linking or agglomeration of solids to occur to form a solid structure such as a catalyst, cross-linking agent or coagulating agent. Alternatively, the liquid medium may be extruded into a solution containing a solidification agent such as a catalyst, cross-linking or coagulating agent or coated onto a substrate and then the composite subjected to conditions to form the solid biocatalyst.

Polymeric materials used to make the biocatalysts may have an organic or inorganic backbone but have sufficient hydrophilic moieties to provide a highly hydrophilic polymer which when incorporated into the matrices exhibits sufficient water sorption properties to provide the sought Hydration Expansion Volume of the biocatalyst. Polymeric materials are also intended to include high molecular weight substances such as waxes (whether or not prepared by a polymerization process), oligomers and the like so long as they form biocatalysts that remain solid under the conditions of the bioconversion process intended for their use and have sufficient hydrophilic properties that the Hydration Expansion Volume can be achieved. As stated above, it is not essential that polymeric materials become cross-linked or further polymerized in forming the polymeric matrix.

Examples of polymeric materials include homopolymers and copolymers which may or may not be cross-linked and include condensation and addition polymers that provide high hydrophilicity and enable the Hydration Expansion Volumes to be obtained. The polymer may be a homopolymer or a copolymer, say, of a hydrophilic moiety and a more hydrophobic moiety. The molecular weight and molecular weight distribution are preferably selected to provide the combination of hydrophilicity and strength as is known in the art. The polymers may be functionalized with hydrophilic moieties to enhance hydrophilicity. Examples of hydrophilic moieties include, but are not limited to hydroxyl, alkoxyl, acyl, carboxyl, amido, and oxyanions of one or more of titanium, molybdenum, phosphorus, sulfur and nitrogen such as phosphates, phosphonates, sulfates, sulfonates, and nitrates, and the hydrophilic moieties may be further substituted with hydrophilic moieties such as hydroxyalkoxides, acetylacetonate, and the like. Typically the polymers contain carbonyl and hydroxyl groups, especially at some adjacent hydrophilic moieties such as glycol moieties. In some instances, the backbone of the polymer contains ether oxygens to enhance hydrophilicity. In some instances, the atomic ratio of oxygen to carbon in the polymer is between about 0.3:1 to 5:1.

Polymers which may find use in forming the matrices include functionalized or non-functionalized polyacrylamides, polyvinyl alcohols, polyetherketones, polyurethanes, polycarbonates, polysulfones, polysulfides, polysilicones, olefinic polymers such as polyethylene, polypropylene, polybutadiene, rubbers, and polystyrene, nylons, polythyloxazyoline, polyethylene glycol, polysaccharides such as sodium alginate, carageenan, agar, hyaluronic acid, chondroitin sulfate, dextran, dextran sulfate, heparin, heparin sulfate, heparan sulfate, chitosan, gellan gum, xanthan gum, guar gum, water soluble cellulose derivatives and carrageenan, and proteins such as gelatin, collagen and albumin, which may be polymers, prepolymers or oligomers, and polymers and copolymers from the following monomers, oligomers and prepolymers: monomethacrylates such as polyethylene glycol monomethacrylate, polypropylene glycol monomethacrylate, polypropylene glycol monomethacrylate, methoxydiethylene glycol methacrylate, methoxypolyethylene glycol methacrylate, methacryloyloxyethyl hydrogen phthalate, methacryloyloxyethyl hydrogen succinate, 3-chloro-2-hydroxypropyl methacrylate, stearyl methacrylate, 2-hydroxy methacrylate, and ethyl methacrylate;

monoacrylates such as 2-hydroxyethyl acrylate, 2-hydroxypropyl acrylate, isobutyl acrylate, t-butyl acrylate, isooctyl acrylate, lauryl acrylate, stearyl acrylate, isobornyl acrylate, cyclohexyl acrylate, methoxytriethylene glycol acrylate, 2-ethoxyethyl acrylate, tetrahydrofurfuryl acrylate, phenoxyethyl acrylate, nonylphenoxypolyethylene glycol acrylate, nonylphenoxypolypropylene glycol acrylate, silicon-modified acrylate, polypropylene glycol monoacrylate, phenoxyethyl acrylate, phenoxydiethylene glycol acrylate, phenoxypolyethylene glycol acrylate, methoxypolyethylene glycol acrylate, acryloyloxyethyl hydrogen succinate, and lauryl acrylate;

dimethacrylates such as 1,3-butylene glycol dimethacrylate, 1,4-butanediol dimethacrylate, ethylene glycol dimethacrylate, diethylene glycol dimethacrylate, triethylene glycol dimethacrylate, polyethylene glycol dimethacrylate, butylene glycol dimethacrylate, hexanediol dimethacrylate, neopentyl glycol dimethacrylate, polyprene glycol dimethacrylate, 2-hydroxy-1,3-dimethacryloxypropane, 2,2-bis-4-methacryloxyethoxyphenylpropane, 3,2-bis-4-methacryloxydiethoxyphenylpropane, and 2,2-bis-4-methacryloxypolyethoxyphenylpropane;

diacrylates such as ethoxylated neopentyl glycol diacrylate, polyethylene glycol diacrylate, 1,6-hexanediol diacrylate, neopentyl glycol diacrylate, tripropylene glycol diacrylate, polypropylene glycol diacrylate, 2,2-bis-4-acryloxyethoxyphenylpropane, 2-hydroxy-1-acryloxy-3-methacryloxypropane; trimethacrylates such as trimethylolpropane trimethacrylate; triacrylates such as trimethylolpropane triacrylate, pentaerythritol triacrylate, trimethylolpropane EO-added triacrylate, glycerol PO-added triacrylate, and ethoxylated trimethylolpropane triacrylate; tetraacrylates such as pentaerythritol tetraacrylate, ethoxylated pentaerythritol tetraacrylate, propoxylated pentaerythritol tetraacrylate, and ditrimethylolpropane tetraacrylate;

urethane acrylates such as urethane acrylate, urethane dimethyl acrylate, and urethane trimethyl acrylate;

amino-containing moieties such as 2-aminoethyl acrylate, 2-aminoethyl methacrylate, aminoethyl methacrylate, dimethyl aminoethyl methacrylate, monomethyl aminoethyl methacrylate, t-butylaminoethylmethacrylate, p-aminostyrene, o-aminostyrene, 2-amino-4-vinyltoluene, dimethylaminoethyl acrylate, diethylaminoethyl acrylate, piperidinoethyl acrylate, piperidinoethyl methacrylate, morpholinoethyl acrylate, morpholinoethyl methacrylate, 2-vinyl pyridine, 3-vinyl pyridine, 2-ethyl-5-vinyl pyridine, dimethylaminopropylethyl acrylate, dimethylaminopropylethyl methacrylate, 2-vinyl pyrrolidone, 3-vinyl pyrrolidone, dimethylaminoethyl vinyl ether, dimethylaminoethyl vinyl sulfide, diethylaminoethyl vinyl ether, 2-pyrrolidinoethyl acrylate, 2-pyrrolidinoethyl methacrylate, and other monomers such as acrylamide, acrylic acid, and dimethylacrylamide.

Not all the above listed polymers will be useful by themselves, but may be required to be functionalized or used to form a co-polymer with a highly hydrophilic polymer.

Cross linking agents, accelerators, polymerization catalysts, and other polymerization additives may be employed such as triethanolamine, triethylamine, ethanolamine, N-methyl diethanolamine, N,N-dimethyl benzylamine, dibenzyl amino, N-benzyl ethanolamine, N-isopropyl benzylamino, tetramethyl ethylenediamine, potassium persulfate, tetramethyl ethylenediamine, lysine, ornithine, histidine, arginine, N-vinyl pyrrolidinone, 2-vinyl pyridine, 1-vinyl imidazole, 9-vinyl carbazole, acrylic acid, and 2-allyl-2-methyl-1,3-cyclopentane dione. For polyvinyl alcohol polymers and copolymers, boric acid and phosphoric acid may be used in the preparation of polymeric matrices. As stated above, the amount of cross-linking agent may need to be limited to assure that the matrices retain high hydrophilicity and the ability to have a high Hydration Expansion Volume. The selection of the polymer and cross-linking agents and other additives to make porous matrices having the physical properties set forth above is within the level of the artisan in the art of water soluble and highly hydrophilic polymer synthesis.

The ME biocatalysts may be formed in the presence of other additives which may serve to enhance structural integrity or provide a beneficial activity for the microorganism such as attracting or sequestering components, providing nutrients, and the like. Additives can also be used to provide, for instance, a suitable density to be suspended in the aqueous medium rather than tending to float or sink. Typical additives include, but are not limited to, starch, glycogen, cellulose, lignin, chitin, collagen, keratin, clay, alumina, aluminosilicates, silica, aluminum phosphate, diatomaceous earth, carbon, polymer, polysaccharide and the like. These additives can be in the form of solids when the polymeric matrices are formed, and if so, are often in the range of about 0.01 to 100 microns in major dimension.

If desired, the biocatalyst may be subjected to stress as is known in the art. Stress may be one or more of starvation, chemical or physical conditions. Chemical stresses include toxins, antimicrobial agents, and inhibitory concentrations of compounds. Physical stresses include light intensity, UV light, temperature, mechanical agitation, pressure or compression, and desiccation or osmotic pressure. The stress may produce regulated biological reactions that protect the microorganisms from shock and the stress may allow the hardier microorganisms to survive while the weaker cells die.

Microorganisms

The ME biocatalyst comprises microorganisms, the microorganisms may be unicellular or may be multicellular that behaves as a single cell microorganism such as filamentous growth microorganisms and budding growth microorganisms. Often the cells of multicellular microorganisms have the capability to exist singularly. The cells can be in any phase of growth, including lag (or conduction), exponential, transition, stationary, death, dormant, vegetative, sporulating, etc. The one or more microorganisms be a psychrophile (optimal growth at −10° C. to 25° C.), a mesophile (optimal growth at 20-50° C.), a thermophile (optimal growth 45° C. to 80° C.), or a hyperthermophile (optimal growth at 80° C. to 100° C.). The one or more microorganisms can be a gram-negative or gram-positive bacterium. A bacterium can be a cocci (spherical), bacilli (rod-like), or spirilla (spiral-shaped; e.g., vibrios or comma bacteria). The microorganisms can be phenotypically and genotypically diverse.

The microorganisms can be a wild-type (naturally occurring) microorganism or a recombinant (including, but not limited to genetically engineered microorganisms) microorganism. A recombinant microorganism can comprise one or more heterologous nucleic acid sequences (e.g., genes). One or more genes can be introduced into a microorganism used in the methods, compositions, or kits described herein, e.g., by homologous recombination. One or more genes can be introduction into a microorganism with, e.g., a vector. The one or more microorganisms can comprise one or more vectors. A vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain a means for self-replication. The vector can, when introduced into a host cell, integrate into the genome of the host cell and replicate together with the one or more chromosomes into which it has been integrated. Such a vector can comprise specific sequences that can allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants. Means of genetically manipulating organisms are described, e.g., Current Protocols in Molecular Biology, last updated Jul. 25, 2011, Wiley, Print ISSN: 1934-3639. In some embodiments, one or more genes involved in byproduct formation are deleted in a microorganism. In some embodiments, one or more genes involved in byproduct formation are not deleted. Nucleic acid introduced into a microorganism can be codon-optimized for the microorganism. A gene can be modified (e.g., mutated) to increase the activity of the resulting gene product (e.g., enzyme). Sought properties in wild-type or genetically modified microorganisms can often be enhanced through a natural modification process, or self-engineering process, involving multigenerational selective harvesting to obtain strain improvements such as microorganisms that exhibit enhanced properties such as robustness in an environment or bioactivity. See, for instance, Ben-Jacob, et al., Self-engineering capabilities of bacteria, J. R. Soc. Interface 2006, 3, doi: 10.1098/rsif.2005.0089, 22 Feb. 2006.

The selected microorganism to be used in a biocatalyst can be targeted to the sought activity. The biocatalysts thus often contain substantially pure strain types of microorganisms and, because of the targeting, enable high bioactivity to be achieved and provide a stable population of the microorganism in the biocatalyst.

The microorganisms used can in many instances of treating wastewater be naturally occurring microorganisms conventionally used for the treatment of such wastewater streams including but not limited to activated sludge. Examples of microorganisms having the capability of oxidizing ammonium cation to nitrite anion include, but are not limited to, *Bacillus amyloliquefaciens; Bacillus pseudofirmus; Arthrobacter globiformis; Rhodococcus rhodnii; Rhodococcus coprophilus; Rhodoferax fermentans; Rhodococcus jostii; Nitrosomonas, Nitrosococcus, Nitrobacter, Nitrospira* and *Nitrococcus* families; *Alcaligenes faecalis; Paracoccus denitrificans; Achromobacter denitrificans; Chromobacterium violaceum; Methylococcus capsulatus; Pseudomonas;* and *Candidatus.*

EXAMPLES

The following examples are provided in illustration of the ME biocatalysts and processes for making the biocatalysts and are not in limitation. All parts and percentages of solids are by mass and of liquids and gases are by volume unless otherwise stated or is clear from the context.

In these examples, the following general procedure is used. The microorganisms for the biocatalyst are grown under suitable planktonic conditions in an aqueous medium for the microorganisms including the presence of nutrients and micronutrients. This medium is referred to herein as the "Culture Medium". The microorganisms used are as available and thus may be either substantially pure strains or mixed cultures. The cell density in the Culture Medium is determined by optical density. If the cell density of the Culture Medium is below that sought to make the biocatalyst, the Culture Medium is centrifuged or filtered to provide a denser, cell-containing fraction. A separately prepared aqueous solution of solubilized precursor is made (referred to herein as the "Polymer Solution"). Any solid additive for the biocatalysts is added to the Polymer Solution in amounts that will provide the sought amount in the biocatalyst. The Polymer Solution is mixed with a mechanical stirrer to assure uniform dispersion of the components in the aqueous medium. Where necessary to solubilize the precursor, the Polymer Solution can be heated as appropriate. In some instances, a micronutrient solution is also added to the Polymer Solution.

Aliquots of each of the Culture Medium (or dense phase from centrifugation) and Polymer Solution are admixed under mechanical stirring at about 30° C. to for a Precursor Solution. Where the microorganism is anaerobic, the Culture Medium and the mixing of the Culture Medium and Polymer Solution and all subsequent steps are maintained under anaerobic conditions by purging with nitrogen.

The Precursor Solution is then extruded through a perforated plate having orifices of about 0.75 millimeter in diameter to form droplets of about 3 millimeters in diameter. The droplets fall into a gently stirred coagulating bath of an aqueous boric acid solution having a pH of about 5. The biocatalyst is recovered from the coagulating bath and washed with distilled water. The biocatalyst, after washing, is placed in a liquid medium containing micronutrients and the substrate under suitable metabolic conditions for the microorganisms.

Table I summarizes the examples. Table II sets forth the microorganisms used in the examples. Table III sets forth the hydrophilic polymer(s) that is used in the examples. Table IV sets forth the solid additive packages used in the examples.

TABLE I

| Example | Polymer Solution | Volume parts Polymer Solution per 100 parts of Precursor Solution | Microorganism | Microorganism culture density wet weight g/L | Volume parts Microorganism culture per 100 parts of Precursor Solution | Solid Additive Package | Mass parts of Solid Additive package per liter of Precursor Solution |
|---|---|---|---|---|---|---|---|
| 1 | Y | 72 | M-13 | 375 | 28 | N/A | N/A |
| 2 | Z | 60 | M-40 | 250 | 40 | S-6 | 1.2 |

TABLE I-continued

| Example | Polymer Solution | Volume parts Polymer Solution per 100 parts of Precursor Solution | Microorganism | Microorganism culture density wet weight g/L | Volume parts Microorganism culture per 100 parts of Precursor Solution | Solid Additive Package | Mass parts of Solid Additive package per liter of Precursor Solution |
|---|---|---|---|---|---|---|---|
| 3 | VVV | 55 | M-13 | 115 | 45 | S-26 | 1.0 |
| 4 | QQ | 40 | M-41 | 65 | 60 | S-13 | 0.7 |
| 5 | NNN | 78 | M-13 | 645 | 22 | N/A | N/A |
| 6 | JJ | 75 | M-41 | 520 | 25 | S-26 | 0.5 |
| 7 | FFF | 72 | M-40 | 470 | 28 | S-13 | 6.2 |
| 8 | J | 78 | M-13 | 665 | 22 | S-23 | 1.2 |
| 9 | F | 76 | M-40 | 580 | 24 | N/A | N/A |
| 10 | K | 77 | M-14 | 575 | 23 | S-27 | 1.0 |
| 11 | CC | 75 | M-41 | 555 | 25 | S-2 | 0.74 |
| 12 | BBB | 73 | M-14 | 435 | 27 | N/A | N/A |
| 13 | SS | 84 | M-13 | 735 | 16 | S-2 | 0.1 |
| 14 | NNN | 36 | M-65 | 65 | 64 | S-26 | 1.0 |
| 15 | TT | 64 | M-57 | 520 | 36 | S-2 | 0.9 |
| 16 | K | 79 | M-37 | 600 | 21 | S-6 | 0.1 |
| 17 | DDD | 50 | M-56 | 285 | 50 | N/A | N/A |
| 18 | R | 40 | M-61 | 200 | 60 | N/A | N/A |
| 19 | K | 77 | M-59 | 65 | 23 | S-6 | 1.2 |
| 20 | Y | 82 | M-62 | 500 | 18 | S-6 | 1.1 |
| 21 | AA | 83 | M-60 | 350 | 17 | S-6 | 1.2 |
| 22 | VVV | 84 | M-58 | 555 | 16 | S-28 | 0.8 |
| 23 | QQ | 92 | M-33 | 250 | 8 | N/A | N/A |
| 24 | M | 89 | M-63 | 265 | 11 | N/A | N/A |
| 25 | AA | 67 | M-64 | 170 | 33 | N/A | N/A |
| 26 | JJ | 40 | M-71 | 195 | 60 | S-2 | 5.0 |
| 27 | FFF | 80 | M-66 | 180 | 20 | S-13 | 1.0 |
| 28 | CC | 82 | M-36 | 555 | 18 | S-26 | 1.0 |
| 29 | R | 49 | M-37 | 700 | 51 | N/A | N/A |
| 30 | NNN | 80 | M-79 | 510 | 20 | N/A | N/A |
| 31 | AA | 94 | M-68 | 145 | 6 | N/A | N/A |
| 32 | K | 74 | M-70 | 145 | 26 | N/A | N/A |
| 33 | TT | 60 | M-67 | 350 | 40 | N/A | N/A |
| 34 | SS | 60 | M-73 | 355 | 40 | N/A | N/A |
| 35 | AA | 50 | M-74 | 155 | 50 | N/A | N/A |
| 36 | VVV | 80 | M-67 | 85 | 20 | N/A | N/A |
| 37 | CC | 88 | M-78 | 95 | 12 | S-2 | 0.5 |
| 38 | K | 62 | M-63 | 205 | 38 | S-6 | 1.0 |
| 39 | TT | 83 | M-70 | 230 | 17 | S-2 | 1.1 |
| 40 | VVV | 83 | M-72 | 400 | 17 | S-29 | 0.5 |
| 41 | AA | 86 | M-72 | 145 | 14 | N/A | N/A |
| 42 | QQ | 41 | M-63 | 245 | 59 | N/A | N/A |
| 43 | K | 76 | M-69 | 430 | 24 | S-2 | 3.0 |
| 44 | M | 80 | M-72 | 205 | 20 | S-26 | 1.2 |
| 45 | R | 80 | M-76 | 280 | 20 | N/A | N/A |
| 46 | M | 40 | M-77 | 85 | 60 | S-2 | 0.9 |
| 47 | AA | 37 | M-66 | 295 | 63 | S-28 | 4.2 |
| 48 | VVV | 40 | M-46 | 590 | 60 | S-6 | 0.5 |
| 49 | Y | 55 | M-37 | 140 | 45 | N/A | N/A |
| 50 | K | 70 | M-75 | 255 | 30 | S-6 | 1.8 |
| 51 | DDD | 80 | M-75 | 255 | 20 | S-26 | 0.3 |
| 52 | K | 70 | M-67 | 255 | 30 | N/A | N/A |
| 53 | K | 67 | M-67 | 100 | 33 | S-25 | 5.5 |
| 54 | R | 72 | M-80 | 75 | 28 | S-2 | 0.9 |

TABLE II

| Microorganism Identifier | Microorganism |
|---|---|
| M-13 | *Nitrosomonas europaea* ATCC ® 19718 ™ |
| M-14 | *Nitrosomonas oceani* ATCC ® 19707 ™ |
| M-40 | *Rhodococcus* sp. ATCC ® 55309 ™ |
| M-41 | *Rhodococcus* sp. ATCC ® 21504 ™ |
| M-56 | *Nitrobacter alkalicus* AN1 |
| M-57 | *Nitrobacter hamburgensis* |
| M-58 | *Nitrobacter vulgaris* |
| M-59 | *Nitrobacter winogradskyi* |
| M-60 | *Nitrococcous* sp. |
| M-61 | *Nitrospira moscoviensis* |
| M-62 | *Nitrospira* sp. |
| M-63 | *Alcaligenes faecalis* |
| M-64 | *Arthrobacter globiformis* |
| M-65 | *Paracoccus denitrificans* ATCC ® 19367 ™ |
| M-37 | *Paracoccus denitrificans* ATCC ® 17741 ™ |
| M-36 | *Achromobacter denitrificans* ATCC ® 15173 ™ |
| M-66 | *Chromobacterium violaceum* |
| M-33 | *Methylococcus capsulatus* ATCC ® 19069 ™ |
| M-67 | *Nitrosomonas cryotolerans* |
| M-68 | *Nitrosomonas eutropha* |
| M-69 | *Nitrosopomilus maritimus* SCM1 |
| M-70 | *Nitrospira briensis* |

TABLE II-continued

| Microorganism Identifier | Microorganism |
|---|---|
| M-71 | *Nitrospira multiformis* |
| M-72 | *Nitrospira tenuis* |
| M-73 | *Pseudomonas fluorescens* |
| M-74 | *Pseudomonas Sp. PB16* |
| M-46 | *Bacillus amyloliquefaciens* ATCC ® 23350 ™ |
| M-75 | *Candidatus Anammoxoglobus* |
| M-76 | *Candidatus Brocadia anammoxidans* |
| M-77 | *Candidatus Kuenenia stuttgartiensis* |
| M-78 | *Candidatus Scalindua brodae* |
| M-79 | *Candidatus Scalindua wagneri* |
| M-80 | *Candidatus Anammoxoglobus* |

TABLE IV

| Solid Additive Package Identifier | Composition |
|---|---|
| S-2 | Clay available as Nanomer ® PGV hydrophilic bentonite from Sigma-Aldrich ® 682659 |
| S-6 | Natural bentonite clay as Cloisite ® 116 from Southern Clay Products/Rockwood Additives |
| S-13 | Starch as available from Sigma-Aldrich ® S4251 |
| S-23 | Chitin as available as Sigma-Aldrich ® C7170 |
| S-25 | Fine ground silica available as MIN-U-SIL ® from U.S. Silica |
| S-26 | Polyethylene powder as MIPELON ™ from Mitsui Chemicals America, Inc. |

TABLE III

| Polymer Solution Identifier | Composition |
|---|---|
| F | 23.0 wt. percent of polyvinyl alcohol available as Elvanol ® 70-03 from Dupont ™ having a degree of hydrolysis of 98-98.8 mol percent; 1.0% wt. percent of anhydrous calcium chloride available as Sigma-Aldrich ® C1016; 0.9 wt. percent of sodium alginate available as Nalgin ™ MV-120 from Ingredient Solutions, Inc. |
| J | 12.0 wt. percent of Poly(acrylamide-co-acrylic acid) potassium salt-cross-linked available as Sigma-Aldrich ® 432776; 2.0 wt. percent of sodium alginate available as Nalgin ™ MV-120 from Ingredient Solutions, Inc. |
| K | 12.0 wt. percent of Poly(acrylamide-co-acrylic acid) potassium salt-cross-linked available as Sigma-Aldrich ® 432776; 0.2 wt. percent of ethylene glycol dimethacrylate available as Sigma-Aldrich ® 335681 |
| M | 12.5 wt. percent of poly(acrylic acid) available as Sigma-Aldrich ® 192023 having an average molecular weight of 2000; 1.0 wt. percent polyaniline available as Sigma-Aldrich ® 577073 |
| R | 18.0 wt. percent of poly(N-isopropylacrylamide) available as Sigma-Aldrich ® 535311 having a molecular weight of 19,000-30,000; 0.95 wt. percent of anhydrous calcium chloride available as Sigma-Aldrich ® C1016 |
| Y | 12.5 wt. percent of polyvinyl alcohol available as Elvanol ® 50-04 from Dupont ™ Inc. having a degree of hydrolysis of 87.0-89.0 mol percent; 3.0 wt. percent of ethylene glycol dimethacrylate available as Sigma-Aldrich ® 335681; 1.0 wt. percent κ-Carrageenan available as Sigma-Alrdich ® 22048 |
| Z | 20.0 wt. percent of Elvanol ® 70-04 polyvinyl alcohol from Dupont, Inc. having a degree of hydrolysis of 98.0-98.8 mol percent; 1.90 wt. percent of sodium alginate available as Nalgin ™ MV-120 from Ingredient Solutions, Inc.; 1.0 wt. percent κ-Carrageenan available as Sigma-Alrdich ® 22048 |
| AA | 3.7 wt. percent of polyethylene oxide available as POLYOX ™ WSR N-80 from Dow, Inc. having an approximate molecular weight of 200,000; 0.5 wt. percent of anhydrous calcium chloride available as Sigma-Aldrich ® C1016; 0.2 wt. percent κ-Carrageenan available as Sigma-Alrdich ® 2204 |
| CC | 25.0 wt. percent of polyethylene-alt-maleic anhydride available as Sigma-Aldrich ® 188050 having an average molecular weight 100,000-500,000; 2.2 wt. percent of polyethylene glycol with an average molecular weight of 200 available as Sigma-Aldrich ® P3015 |
| JJ | 7.7 wt. percent of polyvinyl alcohol available as Poval ® PVA-202E from Kuraray Co., Ltd. ™ having a degree of hydrolysis of 87-89 mol percent; 3.4 wt. percent of medium molecular weight Poly(D-glucosamine) available as Sigma-Aldrich ® 448877 |
| QQ | 40.0 wt. percent of polyvinyl alcohol available as Poval ® PVA-224E from Kuraray Co., Ltd. ™ having a degree of hydrolysis of 80-83 mol percent; 0.7 wt. percent of medium molecular weight Poly(D-glucosamine) available as Sigma-Aldrich ® 448877 |
| SS | 5.6 wt. percent of ethylene vinyl alcohol copolymer available as Exceval ™ HR-3010 from Kuraray Co., Ltd. ™ having a degree of hydrolysis of 99-99.4 mol percent; 0.1 wt. percent of sodium carboxymethyl cellulose with an average molecular weight of 250,000 available as Sigma-Aldrich ® 419311 |
| TT | 6.9 wt. percent of polyethylene oxide available as POLYOX ™ WSR N-80 from Dow, Inc. having an approximate molecular weight of 200,000; 6.0 wt. percent of Poly(2-hydroxyethyl methacrylate) available as Sigma-Aldrich ® P3932 |
| BBB | 15.5 wt. percent of polyvinyl alcohol available as Mowial ® 28-99 from Kuraray Co., Ltd. ™ having a degree of hydrolysis of 99.0-99.8 mol percent and a molecular weight of 145,000; 1.5 wt. percent polyethylene glycol with an average molecular weight of 1450 available as Sigma-Aldrich ® P5402 |
| DDD | 1.0 wt. percent of polyethylene oxide available as POLYOX ™ WSR N-10 from Dow, Inc. having an approximate molecular weight of 100,000; 1.0 wt. percent of medium molecular weight Poly(D-glucosamine) available Sigma-Aldrich ® 448877 |
| FFF | 18.7 wt. percent of polyvinyl alcohol available as Sigma-Aldrich ® 363065 having a degree of hydrolysis of 99+mol percent and a molecular weight of 146,000-186,000; 0.8 wt. percent of polyacrylic acid with an average molecular weight of 1800 available as Sigma-Aldrich ® 323667 |
| NNN | 8.8 wt. percent of polyethylene-alt-maleic anhydride available as Sigma-Aldrich ® 188050 having an average molecular weight 100,000-500,000; 1.0 wt. percent polyethylene glycol with an average molecular weight of 1450 available as Sigma-Aldrich ® P5402 |
| VVV | 10.5 wt. percent of ethylene vinyl alcohol copolymer available as Exceval ™ RS-1717 from Kuraray Co., Ltd. ™ having a degree of hydrolysis of 92-94 mol percent; 2.2 wt. percent of Poly(2-hydroxyethyl methacrylate) available as Sigma-Aldrich ® P3932 |

TABLE IV-continued

| Solid Additive Package Identifier | Composition |
|---|---|
| S-27 | Untreated wheat germ as available as Sigma-Aldrich® W0125 |
| S-28 | Microcrystalline Cellulose as available from Sigma-Aldrich® 1098388 |
| S-29 | Casein from bovine milk as available from Sigma-Aldrich® C7078 |

Each of the above ME biocatalysts is screened in batch tests using secondary effluent from a municipal wastewater treatment plant. The ammonia concentration of the effluent varies depending upon when the sample is taken, but is usually in the range of about 25 to 70 milligrams of ammonia (calculated as N) per liter of water. The pH of the sample is adjusted to about 7.0 to 7.5 for purpose of the batch screening tests. About 0.5 liter of the pH-adjusted effluent at ambient temperature, about 22° C., is placed in a 1 liter glass flask containing a magnetic stirrer, an air sparger and a dissolved oxygen probe. To the flask is added about 50 grams of the ME biocatalyst being screened. The flask is immediately sealed with a stopper having a vent tube that passes the off gas to contact a nitrous oxide detector. The contact between the ME biocatalyst and effluent is continued for about 180 minutes while controlling the air sparge rate to provide a dissolved oxygen concentration of about 2 milligrams per liter. After 180 minutes, duplicate samples of effluent are taken for analysis to determine ammonium, nitrate and nitrite ion concentrations. The detector is also analyzed to determine the presence of nitrous oxide in the off gas. Each of the ME biocatalysts reduces the ammonium concentration with nitrite accounting for over 70 percent of the nitrogen in the bioconverted ammonium and provides a mole ratio of nitrate of nitrite of less than 1:10. The nitrous oxide collected on the nitrous oxide detector is approximately the same as that amount collected by passing ambient air over the detector for the same period of time.

Each of the ME biocatalysts of Examples 1, 9 and 49 are evaluated in a bench-scale, continuous process. A glass, 2 liter bioreactor having a lower, perforated plate is charged with about 200 grams of the ME biocatalyst. A pH adjusted secondary effluent as describe above is fed at the top of the bioreactor to provide about 1.5 liters of occupied volume in the bioreactor, and the pH-adjusted secondary effluent feed rate is maintained to provide a hydraulic residence time of about 40 minutes with treated aqueous solution being withdrawn from the bottom of the bioreactor. The air sparge rate is sufficient to maintain a dissolved oxygen concentration of about 2 milligrams per liter. The off gas is contacted with a nitrous oxide detector. Once achieving steady state, each run is about 24 hours. During the run, samples of the treated effluent are intermittently taken and analyzed for ammonium, nitrate and nitrite concentrations. At the conclusion of the run, the nitrous oxide detector is analyzed. In each run, the ammonium is substantially bioconverted and the mole ratio of nitrate anion to nitrite anions is less than 1:20. The nitrous oxide collected on the nitrous oxide detector is approximately the same as that amount collected by passing ambient air over the detector for the same period of time.

By way of example and not in limitation of the invention, a secondary effluent from a municipal wastewater plant containing about 40 milligrams of ammonia is passed to a bioreactor containing about 20 volume percent of biocatalyst of Example 2. The bioreactor is aerated from the bottom, and the aeration maintains relatively uniform agitation throughout the bioreactor and is at a rate sufficient to provide between about 3 and 4 milligrams of dissolved oxygen per liter. The pH of the secondary effluent ranges between about 7.6 and 8.2, and the alkalinity ranges between about 85 and 130 milliequivalents per liter. The secondary effluent is provided to the bioreactor at rates varying from an empty bed contact time (hydraulic retention time excluding the volume of the biocatalyst) of between 2 and 6 hours. Over a duration of nine months of operation, the ammonia concentration in the effluent was about 1 to 15 milligrams per liter, with the highest concentration occurring at an empty bed contact time of 2 hours. The mole ratio of nitrate anion to nitrite anion typically was less than 1:10 regardless of the empty bed contact time. Higher pH and higher alkalinity tend to provide the higher mole ratios of nitrate anion to nitrite anion. A nitrous oxide detector is exposed about 30 centimeters above the water level within the bioreactor for thirty minutes during a period where the empty bed contact time is about 4 hours. The detector is then analyzed for sorbed nitrous oxide. The level of nitrous oxide sorption is approximately the same as that from a control nitrous oxide detector positioned sufficiently away from the bioreactor to not be affected by the off gases from the nitritation.

The nitrous oxide detectors contain molecular sieves to sorb the nitrous oxide in the gases contacting the detector. The nitrous oxide is then desorbed and the amount of nitrous oxide ascertained by gas chromatography.

It is claimed:

1. A process for the nitritation of ammonia in an aqueous medium using ammonia-oxidizing nitrifier microorganisms to bioconvert ammonia comprising:
   contacting the aqueous medium under aerobic conditions at a temperature of from about 0° C. to 50° C. with biocatalyst, said biocatalyst comprising:
   a. a solid structure of hydrated hydrophilic polymer defining an interior structure having a plurality of interconnected major cavities having a smallest dimension of between 5 and 100 microns and a Hydration Expansion Volume (HEV), which is calculated in volume percent, of 1000 or more, and
   b. a population of microorganisms substantially irreversibly retained in the interior structure, said population of microorganisms being in a concentration of about 60 grams or more per liter based upon the volume defined by the exterior of the solid structure when fully hydrated, wherein the microorganisms maintain their population as substantially stable,
   for a time sufficient to oxidize at least a portion of the ammonia to nitrite anion and provide a nitrite-containing effluent and an off-gas, wherein a sufficient amount of biocatalyst is used such that less than about 0.25 percent of the bioconverted ammonia calculated on an atomic N basis is emitted as nitrous oxide into the off-gas.

2. The process of claim 1 wherein at least about 40 percent of the ammonia calculated on an atomic N basis is converted to nitrite anion.

3. The process of claim 1 wherein the aqueous medium is derived from an industrial wastewater stream.

4. The process of claim 1 wherein the aqueous medium is derived from an anaerobic digestion wastewater stream.

5. The process of claim 1 wherein the aqueous stream contains organic carbon, and organic carbon is converted to carbon dioxide during the contact of the aqueous stream with the biocatalyst.

6. The process of claim 1 wherein the aqueous stream is pretreated to remove organic carbon prior to the contact with the biocatalyst containing ammonia oxidizing microorganisms.

7. The process of claim 1 wherein at least about 90 percent of the ammonia oxidized is nitrite anion (calculated on an atomic N basis).

8. The process of claim 1 wherein the nitrite-containing effluent is subjected to bacterial denitrification to produce dinitrogen and provide a denitrification effluent.

9. The process of claim 8 wherein ammonia is the reducing equivalents and is oxidized to dinitrogen.

10. The process of claim 9 wherein the denitrification effluent contains less than about 5 parts per million total nitrogen per liter.

11. A method for enhancing bioactivity of a biocatalyst containing ammonia-oxidizing, microorganisms for the nitritation of ammonia-containing aqueous media, said biocatalyst comprising:
  a. a solid structure of hydrated hydrophilic polymer defining an interior structure having a plurality of interconnected major cavities having a smallest dimension of between 5 and 100 microns and a Hydration Expansion Volume (HEV), which is calculated in volume percent, of 1000 or more, and
  b. a population of said microorganisms substantially irreversibly retained in the interior structure, said population of microorganisms being in a concentration of about 60 grams or more per liter based upon the volume defined by the exterior of the solid structure when fully hydrated, wherein the microorganisms maintain their population as substantially stable, comprising contacting said biocatalyst with an ammonia-containing aqueous medium under metabolic conditions including a presence of at least about 5 milligrams of dissolved oxygen per liter for a time sufficient to increase the bioactivity of the biocatalyst for nitritation.

12. The method of claim 11 wherein the contact is in the range of between about 2 and 50 hours.

13. A continuous process for the nitritation of ammonia in an aqueous medium using ammonia-oxidizing nitrifier microorganisms comprising:
  a. continuously feeding said aqueous medium to at least one bioreaction zone containing biocatalyst wherein said aqueous medium is contacted under aerobic conditions at a temperature of from about 0° C. to 50° C. and at a pH greater than 7 with said biocatalyst to provide a treated aqueous medium containing nitrite anion, said biocatalyst comprising:
    i. a solid structure of hydrated hydrophilic polymer defining an interior structure having a plurality of interconnected major cavities having a smallest dimension of between 5 and 100 microns and a Hydration Expansion Volume (HEV), which is calculated in volume percent, of 1000 or more, and
    ii. a population of microorganisms substantially irreversibly retained in the interior structure, said population of microorganisms being in a concentration of about 60 grams or more per liter based upon the volume defined by the exterior of the solid structure when fully hydrated, wherein the microorganisms maintain their population as substantially stable; and
  b. continuously withdrawing from said at least one bioreaction zone said treated aqueous medium,
  wherein a combination of pH of said aqueous medium is sufficiently above 7 and duration of contact of said aqueous medium in the at least one bioreaction zone containing biocatalyst is sufficiently brief that that the treated aqueous medium contains greater than about 1 milligram of ammonium cation per liter, to provide a treated aqueous medium having a mole ratio of nitrate anion to nitrite anion less than about 1:8.

14. The process of claim 13 wherein the pH of the aqueous medium in the bioreaction zone is at least 7.3.

15. The process of claim 13 wherein the alkalinity is greater than 50 milliequivalents per liter.

16. The process of claim 13 wherein the nitrate-containing effluent is subjected to microbial denitrification to produce dinitrogen and provide a denitrification effluent.

17. The process of claim 16 wherein ammonia is a reducing equivalent and is oxidized to dinitrogen.

18. A continuous process for the nitritation of ammonia in an aqueous medium using ammonia-oxidizing nitrifier microorganisms wherein at least one of the volumetric flow of the aqueous medium and concentration of ammonium cation in said aqueous medium changes over time, comprising:
  a. continuously feeding said aqueous medium to one or more bioreaction zones containing biocatalyst wherein said aqueous medium is contacted under aerobic conditions at a temperature of from about 0° C. to 50° C. with said biocatalyst to provide a treated aqueous medium containing nitrite anion, said biocatalyst comprising:
    i. a solid structure of hydrated hydrophilic polymer defining an interior structure having a plurality of interconnected major cavities having a smallest dimension of between 5 and 100 microns and a Hydration Expansion Volume (HEV), which is calculated in volume percent, of 1000 or more, and
    ii. a population of microorganisms substantially irreversibly retained in the interior structure, said population of microorganisms being in a concentration of about 60 grams or more per liter based upon the volume defined by the exterior of the solid structure when fully hydrated,
  wherein the microorganisms maintain their population as substantially stable; and
  b. continuously withdrawing from said one or more bioreaction zones said treated aqueous medium,
  wherein a combination of pH of said aqueous medium is sufficiently above 7 and duration of contact of said aqueous medium in the at least one bioreaction zone containing biocatalyst is controlled such that that the treated aqueous medium contains greater than about 1 milligram of ammonium cation per liter, to provide a treated aqueous medium having a mole ratio of nitrate anion to nitrite anion less than about 1:8.

19. The process of claim 18 wherein at least two bioreaction zones are provided in parallel flow relationship and the control is effected through changing the number of parallel bioreaction zones to which the aqueous medium is fed.

20. The process of claim 18 wherein said control is effected by changing the volume of one or more bioreaction zones.

* * * * *